United States Patent [19]

Woo et al.

[11] Patent Number: 5,962,631
[45] Date of Patent: Oct. 5, 1999

[54] 2, 7-ARYL-9-SUBSTITUTED FLUORENES AND 9-SUBSTITUTED FLUORENE OLIGOMERS AND POLYMERS

[75] Inventors: Edmund P. Woo, Midland; William R. Shiang, Sanford; Michael Inbasekaran; Gordon R. Roof, both of Midland, all of Mich.

[73] Assignee: The Dow Chemical Company, Midland, Mich.

[21] Appl. No.: 08/994,187

[22] Filed: Dec. 19, 1997

Related U.S. Application Data

[63] Continuation of application No. 08/508,942, Jul. 28, 1995, Pat. No. 5,708,130.

[51] Int. Cl.$^6$ .................................................. C08G 61/00
[52] U.S. Cl. ........................... 528/397; 528/401; 521/82; 478/421; 478/690; 478/917; 427/407.1; 313/483
[58] Field of Search ...................................... 528/397, 401; 521/82; 428/421, 690, 917; 427/407.1; 313/483

[56] References Cited

U.S. PATENT DOCUMENTS

| | | |
|---|---|---|
| 3,641,115 | 2/1972 | Peck et al. .............................. 260/475 |
| 4,769,292 | 9/1988 | Tang et al. . |
| 5,621,131 | 4/1997 | Kreuder et al. . |

FOREIGN PATENT DOCUMENTS

| | | |
|---|---|---|
| 0 707 020 | 4/1996 | European Pat. Off. . |
| 2702870 | 9/1994 | France . |
| 96/00983 | 1/1996 | WIPO . |
| 97/05104 | 2/1997 | WIPO . |

OTHER PUBLICATIONS

Chemical Abstract 126:322721 (1997).
Chemical Abstracts, 59, 15231 (1963).
Chemical Abstracts, 67, 64085x (1967).
Derwent 94–307586/38 (JP06234668–A), p. 119, Week 9438.
Adachi, Chihaya, "Blue Light–Emitting Organic Electroluminescent Devices", Appl. Phys. Lett., vol. 56, No. 9, pp. 799–801 (1990).
Braun, D., et al., "Visible Light Emission From Semiconducting Polymer Diodes", Appl. Phys. Lett., vol. 58, No. 18, pp. 1982–1984 (1991).
Brown, Charles Eric, "Polynuclear and Halogenated Structures in Polyphenylenes Synthesized form Benzene, Biphenyl, and p–Terphenyl Under Various Conditions: Characterization by Laser Desorption/Fourier Transform Mass Spectrometry", Journal of Polymer Science: Polymer Chemistry Edition, vol. 24, pp. 255–267 (1986).
Burroughes, J. H., et al., "Light–Emitting Diodes Based on Conjugated Polymers", Nature, vol. 347, p. 539–541 (1990).
Burrows, P. E., et al., "Metal Ion Dependent Luminescence Effects in Metal Tris–Quinolate Organic Heterojunction Light Emitting Devices", Appl. Phys. Lett., vol. 64, No. 20, pp. 2718–2720 (1994).

Colon, Ismael, et al., "Coupling of Aryl Chlorides by Nickel and Reducing Metals", J. Org. Chem., vol. 51, No. 14, pp. 2627–2637 (1986).
Colon, I., et al., "High Molecular Weight Aromatic Polymers by Nickel Coupling of Aryl Polychlorides", Journal of Polymer Science: Part A: Polymer Chemistry, vol. 28, pp. 367–383 (1990).
Fuji, A., et al., "Color–Variable Electroluminescent Diode with Single Quantum Well Structure Utilizing 8–Hydroxyquinaline Aluminum and Aromatic Diamine", Jpn. J. Appl. Phys., vol. 34, pp. 499–502 (1995).
Fukuda, Masahiko, et al., "fusible Conducting Poly(9–alkylfluorene) and Poly(9,9–dialkylfluorene) and Their Characteristics", Jpn. J. Appl. Phys., vol. 28, No. 8, pp. 1433–1435 (1989).
Fukuda, Masahiko, et al., "Synthesis of Fusible and Soluble Conducting Polyfluorene Derivatives and Their Characteristics", Journal of Polymer Science: Part A: Polymer Chemistry, vol. 31, pp. 2465–2471 (1993).
Ghera, E., et al., "Reactions of Active Methylene Compounds in Pyridine Solution. II. Aldol–type Reactions of Indene and Fluorene", J. Amer. Chem. Soc., vol. 82, pp. 4945–4952 (1960).
Grem, G., et al., "Realization of a Blue–Light–Emitting Device using Poly(p–phenylene)", Adv. Materials, vol. 4, pp. 36–37 (1992).
Hamada, Yuji, et al., "High Luminance in Organic Electroluminescent Devices with Bis(10–hyudroxybenzo[h]quinolinato)beryllium as an Emitter", Chemistry Letters, pp. 905–906 (1993).
Hamada, Yuji, et al., "Organic Electroluminescent Devices with Bright Blue Emission", Optoelectronics—Devices and Technologies, vol. 7, No. 1, pp. 83–93 (1992).

(List continued on next page.)

*Primary Examiner*—Duc Truong
*Attorney, Agent, or Firm*—Ann K. Galbraith

[57] ABSTRACT

The invention relates to 2,7-substituted-9-substituted fluorenes and 9-substituted fluorene oligomers and polymers. The fluorenes, oligomers and polymers are substituted at the 9-position with two hydrocarbyl moieties which may optionally contain one or more of sulfur, nitrogen, oxygen, phosphorous or silicon heteroatoms; a $C_{5-20}$ ring structure formed with the 9-carbon on the fluorene ring or a $C_{4-20}$ ring structure formed with the 9-carbon containing one or more heteroatoms of sulfur, nitrogen or oxygen; or a hydrocarbylidene moiety. In one embodiment, the fluorenes are substituted at the 2- and 7-positions with aryl moieties which may further be substituted with moieties which are capable of crosslinking or chain extension or a trialkylsiloxy moiety. The fluorene polymers and oligomers may be substituted at the 2- and 7'-positions. The monomer units of the fluorene oligomers and polymers are bound to one another at the 2- and 7'-positions. The 2,7'-aryl-9-substituted fluorene oligomers and polymers may be further reacted with one another to form higher molecular weight polymers by causing the optional moieties on the terminal 2,7'-aryl moieties, which are capable of crosslinking or chain extension, to undergo chain extension or crosslinking. Also disclosed are processes for preparing the disclosed compounds.

11 Claims, No Drawings

OTHER PUBLICATIONS

Iyoda, Masahiko, et al., "Homocoupling of Aryl Halides Using Nickel(II) Complex and Zinc in the Presence of Et$_4$NI. An Efficient Method for the Synthesis of Biaryls and Bipyridines", Bull. Chem. Soc. Jpn., vol. 63, pp. 80–87 (1990).

Kido, Junji, et al., "Blue Electroluminescent 1,2,4–Triazole Deriative", Chemistry Letters, pp. 47–48 (1996).

Kido, J., et al., "Single–Layer White Light–Emitting Organic Electroluminescent Devices Based on Dye–Dispersed Poly(N–vinylcarbazole)", Appl. Phys. Lett., vol. 67, No. 16, pp. 2281–2283 (1995).

Larmat F., et al., "Electrochemical and Electronic Properties of Poly[bis(2–thienyl)–9,9'–didecylfluorene] and Poly[bis(2–(3,4–ethylenedioxy)thienyl)–9,9'–didecylfluorene]", Amer. Chem. Soc., vol. 37, No. 1, pp. 799–800 (1997).

Li, Xiao–Chang, et al.,. "Synthesis and Optoelectronic Properties of Aromatic Oxadiazole Polymers", J. Chem. Soc., Chem. Commun., pp. 2211–2212 (1995).

Miyaura, Norio, et al., "Palladium–Catalyzed Cross–Coupling Reactions of Organoboron Compounds", Chem. Rev. vol. 95, No. 7, pp. 2457–2483 (1995).

Miyaura, N., et al., "The Palladium–Catalyzed Cross–Coupling Reaction of Phenylboronic Acid with Haloarenes in the Presence of Bases", Synthetic Communications, vol. 11, No. 7, pp. 513–519 (1981).

O'Brien, D., et al., "Electroluminescence Applications of a Poly(phenyl quinoxaline)", Synthetic Metals, vol. 76, pp. 105–108. (1996).

Ohmori, Yutaka, et al., "Blue Electroluminescent Diodes Utilizing Poly(alkylfluorene)", Jpn. J. of Appl. Phys., vol. 30, No. 11B, pp. L1941–L1943 (1991).

Ohmori, Yutaka, et al., "Carrier Transport in a Three–Layered Electroluminescent Device", J. Phys. D: Appl. Phys., vol. 29, pp. 2983–2987 (1996).

Ohmori, Yutaka, et al., "Enhancement of Emission Efficiency in Electroluminescent Diode Utilizing Vapor–Deposited Poly(alkylflourene)", Jpn. J. Appl. Phys., vol. 32, No. 11B, pp. L1663–L1666 (1993).

Ohmori, Yutaka, et al., "Visible–Light Electroluminescent Diodes Utilizing Poly(3–alkylthiophene)", Jpn. J. Appl. Phys., vol. 30, No. 11B. pp. L1938–L1940 (1991).

Remmers, Marcus, et al., "Synthesis, Optical Absorption and Fluorescence of New Poly(p–phenylene)–Related Polymers", Macromol. Rapid Commun., vol. 17, pp. 239–252 (1996).

Strukelj, Marko, et al., "Design and Application of Electron–Transporting Organic Materials", Science, vol. 267, pp. 1969–1972 (1995).

Tang, C. W., et al., "Electroluminescence of Doped Organic Thin Films", J. Appl. Phys., vol. 65, No. 9, pp. 3610–3616 (1989).

Tang, C. W., et al., "Organic Electrolumininescent Diodes", Appl. Phys. Lett., vol. 51, No. 12, pp. 913–915 (1987).

Uchida, M. et al., "Color–Variable Light–Emitting Diode Utilizing Conducting Polymer Containing Fluorescent Dye", Jpn. J. Appl. Phys., vol. 32, pp. L 921–L 924 (1993).

Wallow, Thomas I., et al., "Highly Efficient and Accelerated Suzuki Aryl Couplings Mediated by Phosphine–Free Palladium Sources", J. Org. Chem., vol. 59, No. 17, pp. 5034–5037 (1994).

Wallow, Thomas I., et al., "In Aqua Synthesis of Water–Soluble Poly(p–phenylene) Derivatives", J. Am. Chem. Soc., vol. 115, pp. 7412–7414 (1991).

Wallow, Thomas I., et al., "Palladium–mediated Poly(p–phenylene) Synthesis: Evidence for a Molecular Weight Limiting Phosphine Arylation Reaction", Polymer Preprints, vol. 34, No. 1 (1993).

Weaver, M. S., et al., "Recent Progress in Polymers for Electroluminescence: Microcavity Devices and Electron Transport Polymers", Thin Solid Films, vol. 273, pp. 39–47 (1996).

Wu, C. C. et al., "Poly(p–phenylene Vinylene)/Tris(8–hydroxy) Quinoline Aluminum Heterostructure Light Emitting Diode", Appl. Phys. Lett., vol. 66, No. 6, pp. 653–655 (1995).

Yamamoto, Takakazu, "Electrically Conducting and Thermally Stable–Conjugated Poly(Arylene)s Prepared by Organometallic Processes", Prog. Polym. Sci., vol. 17, pp. 1153–1205 (1992).

Yang, Kang, et al., "Novel Carbon Catalysis: Oxidation in Basic Solution", Journal of Organic Chemistry, vol. 58, p. 3754 (1958).

Yang, Yang, et al., "Efficient Blue–Green and White Light–Emitting Electrochemical Cells Based on Poly[9,9–bis(3, 6–dioxaheptyl)–fluorene–2,7–diyl]", J. Appl. Phys., vol. 81, No. 7, pp. 3294–3298 (1997).

Yang, Y., et al., "Electron Injection Polymer for Polymer Light–Emitting Diodes", J. Appl. Phys., vol. 77, No. 9, pp. 4807–4809 (1995).

Yoshida, Masayoshi, "Three–Layered Multicolor Organic Electroluminescent Device", Appl. Phys. Lett. vol. 69, No. 6, pp. 734–736 (1996).

Chemical Abstract 97:514256/48, WO97/39045 (1997).

Chemical Abstract 97:558577/51, WO97/39082 (1997).

2,7-ARYL-9-SUBSTITUTED FLUORENES AND 9-SUBSTITUTED FLUORENE OLIGOMERS AND POLYMERS

This application is a Continuation of prior application Ser. No. 08/508,942, filed on Jul. 28, 1995, now U.S. Pat. No. 5,708,130.

This invention relates to 2,7-aryl-9-substituted fluorenes and 9-substituted fluorene oligomers and polymers prepared therefrom. The invention further relates to processes for the preparation of such fluorenes, oligomers and polymers. The invention also relates to films and coatings prepared from such fluorenes, oligomers and polymers and processes for preparing such films and coatings.

Polymers and oligomers of fluorenes substituted by alkyl groups at the 9-carbon position have been reported by Fukuda et al., *Japanese Journal of Applied Physics*, Vol. 28, pp. L1433–L1435 (1989). These polymers were prepared by the Kovacic procedure wherein the appropriate fluorene monomers were treated for several days with a large excess of oxidizing metal salts such as ferric chloride. The structures are represented as poly(fluorene-2,7'-diyls). In a later article, Fukuda discloses that the procedure used resulted in significant crosslinking and mislinking reactions during the polymerization. See Fukuda et al., *Journal of Polymer Science*, Polymer Chemistry Edition, Vol. 31, pp. 2465–2471 (1993). Brown et al., *Journal of Polymer Science*, Polymer Chemistry Edition, Vol. 24, pp. 255–267 (1989) disclose the presence of substantial chemical defects under the reaction conditions of the Kovacic procedure, in particular, a significant number of polynuclear structures and substitutions at positions other than the 2,7-position result. In addition, the oxidative polymerization is not regiospecific and the coupling of fluorenes through other positions, such as the 3,5'- and 3,6'-positions, frequently occurs. In addition, it is possible that branching may occur as a result of attachment of more than two other fluorene molecules to a given fluorene molecule, thereby creating trifunctional materials which could crosslink during the reparation process. The presence of such by-products can result in low molecular weight oligomers and polymers with low degrees of polymerization. Further, such materials demonstrate a high polydispersity and low glass transition temperatures. Such problems result in poor film formation properties and poor properties in any films prepared in that such films may demonstrate unacceptable mechanical properties and low heat resistance. Furthermore, the oxidative coupling process is very slow.

Fukuda et al., supra, disclose that the poly(9-alkylfluorenes-2,7'-diyls) may be used to prepare polymeric light-emitting diode devices. The materials prepared according to the teachings of Fukuda demonstrate low heat resistance and a low degree of polymerization. Thus, light-emitting diode devices using such materials would demonstrate inferior durability.

In order to successfully prepare such materials on a commercial scale, a faster and more efficient process for the preparation of such materials is needed. What is further needed are 9-substituted fluorenes which enable the preparation of polymers having low polydispersity, high molecular weights and degrees of polymerization. Further, what is needed are such materials which can readily prepare films which have high solvent and heat resistance. What is further needed are such materials which have such properties and continue to demonstrate good fluorescence ability. What is further needed is a procedure for the preparation of such materials. What is also needed are procedures for preparing high heat resistant and solvent resistant films from such materials.

SUMMARY OF THE INVENTION

The invention relates to 2,7-substituted-9-substituted fluorenes and 9-substituted fluorene oligomers and polymers. The fluorenes, oligomers and polymers are substituted at the 9-position with two hydrocarbyl moieties which may optionally contain one or more of sulfur, nitrogen, oxygen, phosphorous or silicon heteroatoms; a $C_{5-20}$ ring structure formed with the 9-carbon on the fluorene ring or a $C_{4-20}$ ring structure formed with the 9-carbon containing one or more heteroatoms of sulfur, nitrogen or oxygen; or a hydrocarbylidene moiety. In one embodiment, the fluorenes are substituted at the 2- and 7-positions with aryl moieties which may further be substituted with moieties which are capable of crosslinking or chain extension or a trialkylsiloxy moiety. The fluorene polymers and oligomers may be substituted at the 2- and 7'-positions. The monomer units of the fluorene oligomers and polymers are bound to one another at the 2- and 7'-positions. The 2,7'-aryl-9-substituted fluorene oligomers and polymers may be further reacted with one another to form higher molecular weight polymers by causing the optional moieties on the terminal 2,7'-aryl moieties, which are capable of crosslinking or chain extension, to undergo chain extension or crosslinking.

In another embodiment, the invention relates to 9-substituted fluorene oligomers and polymers which are terminated at the terminal 2- and 7'-positions with a hydrogen or halogen wherein the oligomers and polymers have weight average molecular weights of about 10,000 or greater and polydispersities of about 3.0 or less.

The polymers and oligomers do not contain a significant amount of misformed polynuclear structures or bonding through positions other than the 2- and 7'-positions. The fluorene polynuclear rings can further be substituted at the 3-, 4-, 5- or 6-positions with substituents which do not adversely affect the properties of the 2,7-aryl-9-substituted fluorenes or 9-substituted fluorene oligomers and polymers or subsequent processing of such materials for their intended uses.

Another embodiment of the invention involves a process for the preparation of 2,7-aryl-9-substituted fluorenes and 9-substituted fluorene oligomers and polymers. The process comprises contacting one or more 2,7-dihalo-9-substituted fluorenes with a haloaromatic compound or haloaromatic compounds, being further substituted with a reactive group capable of crosslinking or chain extension or a trialkylsiloxy moiety, in the presence of a catalytic amount of a divalent nickel salt, at least a stoichiometric amount of zinc powder and a trihydrocarbylphosphine in a polar solvent, under conditions such that a 2,7-aryl-9-substituted fluorene or a 9-substituted fluorene oligomer or polymer is prepared. The 9-substituted fluorene oligomers and polymers terminated at the terminal 2- and 7'-positions with hydrogen or a halogen are prepared by the process described above in the absence of a haloaromatic compound.

In another embodiment, the invention comprises films or coatings comprising 2,7-aryl-9-substituted fluorenes or 9-substituted fluorene oligomers or polymers. Such films may be prepared by applying a composition comprising the 2,7-aryl-9-substituted fluorenes or 9-substituted fluorene oligomers or polymers to a substrate and exposing the applied composition to conditions such that a film is prepared.

Further, the 2,7-aryl-9-substituted fluorenes or 9-substituted fluorene oligomers or polymers may be B-staged, partially crosslinked or chain extended, to prepare a composition which may be used to prepare coatings or films as described hereinbefore.

The 2,7-aryl-9-substituted fluorenes or 9-substituted fluorene oligomers or polymers demonstrate fluorescence, high glass transition temperatures or liquid-crystalline properties and facilitate the preparation of films which have high heat resistance and solvent resistance. The 9-substituted fluorene oligomers and polymers demonstrate low polydispersities. Polymers based on 2,7-aryl-9-substituted fluorenes and 9-substituted fluorene oligomers and polymers which have high molecular weights can be prepared if desired. The 2,7-aryl-9-substituted fluorenes or 9-substituted fluorene oligomers or polymers may be used to prepare films or coatings which may be used in polymeric light-emitting diodes, preferably as the emitting layer. Additionally, such films or coatings may be used as protective layers in electronic devices or as fluorescent coatings in a wide variety of uses.

DETAILED DESCRIPTION OF THE INVENTION

In a preferred embodiment, the 2,7-aryl-9-substituted fluorenes and 9-substituted fluorene oligomers or polymers correspond to Formula 1,

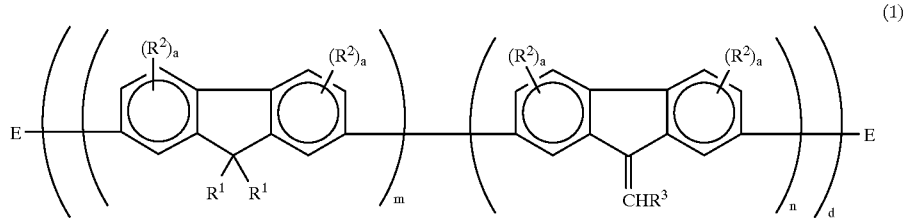

wherein substantially all of the monomer units are connected to end moieties or other monomer units through the 2- and 7-carbon atoms.

In Formula 1, E is halogen, hydrogen or an aryl moiety which may optionally be substituted with a reactive group capable of undergoing chain extension or crosslinking or a trialkylsiloxy. As used herein, a reactive group capable of undergoing chain extension or crosslinking refers to any group which is capable of reacting with another of the same group or another group so as to form a link to prepare oligomers or polymers. Preferably, such reactive group is a hydroxy, glycidyl ether, acrylate ester, methacrylate ester, ethenyl, ethynyl, maleimide, nadimide, trifluorovinyl ether moiety or a cyclobutene moiety fused to one of the aromatic rings. E is preferably halogen, aryl or aryl substituted with a reactive group capable of undergoing chain extension or crosslinking or a trialkylsiloxy moiety. E is even more preferably aryl or aryl substituted with a reactive group capable of undergoing chain extension or crosslinking or a trialkylsiloxy. E is most preferably phenol, a cyano-substituted phenyl or a benzylcyclobutene moiety.

$R^1$ is independently in each occurrence $C_{1-20}$ hydrocarbyl or $C_{1-20}$ hydrocarbyl containing one or more heteroatoms of S, N, O, P or Si or both of $R^1$ together with the 9-carbon on the fluorene may form a $C_{5-20}$ ring structure or a $C_{4-20}$ ring structure containing one or more heteroatoms of S, N, or O. Preferably, $R^1$ is $C_{1-12}$ alkyl, $C_{6-10}$ aryl or alkyl-substituted aryl, $C_{4-16}$ hydrocarbyl carboxylate or $(C_{9-16}$ aryl) trialkylsiloxy moiety. In the embodiment where the two $R^1$ form a ring structure with the 9-carbon atom of the fluorene ring, the ring structure formed is preferably a $C_{5-20}$ straight- or branched-ring structure or a $C_{4-20}$ straight- or branched-chain ring structure containing one or more heteroatoms of S, N or O; even more preferably a $C_{5-10}$ aliphatic ring or a $C_{4-10}$ aliphatic ring containing one or more of S or O; and most preferably a $C_{5-10}$ cycloalkyl or $C_{4-10}$ cycloalkyl containing oxygen.

$R^2$ is independently in each occurrence $C_{1-20}$ hydrocarbyl, $C_{1-20}$ hydrocarbyloxy, $C_{1-20}$ thioether, $C_{1-20}$ hydrocarbyloxycarbonyl, $C_{1-20}$ hydrocarbylcarbonyloxy or cyano. $R^2$ is preferably $C_{1-12}$ alkyl, $C_{6-10}$ aryl or alkyl-substituted aryl, $C_{6-10}$ aryloxy or alkyl-substituted aryloxy, $C_{1-12}$ alkoxycarbonyl, $C_{6-10}$ aryloxycarbonyl or alkyl-substituted aryloxycarbonyl, $C_{1-12}$ alkoxy, $C_{1-12}$ alkylcarbonyloxy, $C_{6-10}$ arylcarbonyloxy or alkyl-substituted arylcarbonyloxy, cyano or $C_{1-20}$ alkylthio. Even more preferably, $R^2$ is $C_{1-4}$ alkoxy, phenoxy, $C_{1-4}$ alkyl, phenyl or cyano.

$R^3$ is independently in each occurrence $C_{1-20}$ hydrocarbyl or $C_{1-20}$ hydrocarbyl substituted with di($C_{1-20}$ alkyl)amino, $C_{1-20}$ hydrocarbyloxy or $C_{1-20}$ hydrocarbyl or tri($C_{1-10}$ alkyl)siloxy. $R^3$ is preferably a $C_{1-20}$ straight- or branched-chain aliphatic, a $C_{1-20}$ straight- or branched-chain aliphatic containing one or more cycloaliphatic rings or a phenyl moiety and such moiety may optionally be substituted with a di($C_{1-20}$ alkyl)amino, $C_{1-20}$ hydrocarbyl, tri($C_{1-10}$ alkyl) siloxy or $C_{1-20}$ hydrocarbyloxy moiety. $R^3$ is more preferably a $C_{3-10}$ aliphatic, a $C_{3-10}$ aliphatic containing one or more cycloaliphatic moieties, phenyl or phenyl substituted with di($C_{1-12}$ alkyl)amino, $C_{1-10}$ alkoxy, $C_{6-10}$ aryloxy or alkyl-substituted aryloxy, $C_{1-10}$ alkyl or $C_{6-10}$ aryl or alkyl-substituted aryl or tri($C_{1-4}$ alkyl)siloxy. Even more preferably, $R^3$ is phenyl or phenyl substituted with di($C_{1-6}$ alkyl)amino, $C_{1-10}$ alkoxy or $C_{1-10}$ alkyl.

a is independently in each occurrence from about 0 to about 1. m is independently in each occurrence a number of from about 1 to about 20. n is independently in each occurrence a number of from about 0 to about 20. d is a number of from about 1 to about 100.

In a preferred embodiment, the 2,7-aryl-9-substituted fluorenes and 9-substituted fluorene oligomers or polymers correspond to Formula 2,

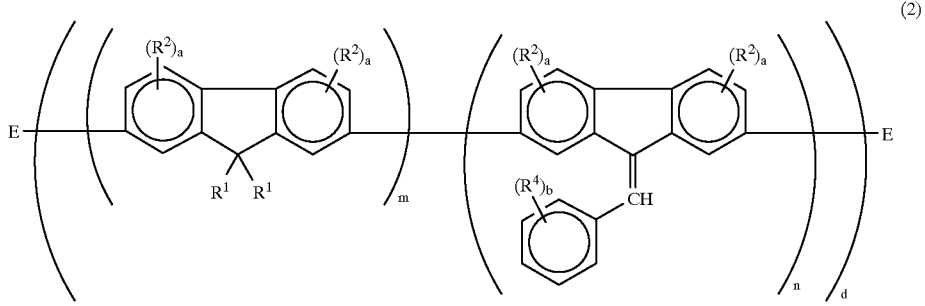

(2)

wherein $R^1$, $R^2$, a, d, m and n are as defined hereinbefore. $R^4$ is independently in each occurrence di($C_{1-20}$ alkyl)amino, $C_{1-20}$ hydrocarbyloxy, tri($C_{1-10}$ alkyl)siloxy or $C_{1-2}$ hydrocarbyl. b is independently in each occurrence a number of from about 0 to about 3.

$R^4$ is preferably di($C_{1-2}$ alkyl)amino, $C_{1-10}$ alkoxy, $C_{6-10}$ aryloxy or alkyl-substituted aryloxy, tri($C_{1-4}$ alkyl)siloxy $C_{1-10}$ alkyl or $C_{6-10}$ aryl or alkyl-substituted aryl. Even more preferably, $R^4$ is di($C_{1-6}$ alkyl)amino, $C_{1-10}$ alkoxy or $C_{1-10}$ alkyl. Preferably, b is about 0 to about 2, and most preferably b is 1.

m is preferably a positive number of about 0 or greater and more preferably about 1 or greater and preferably about 10 or less, more preferably about 5 or less and most preferably about 2 or less. n is the number of from about 0 or more and more preferably about 1 or more and preferably about 10 or less, more preferably about 5 or less and most preferably about 2 or less. d is a number of about 1 or greater, more preferably about 3 or greater and most preferably about 10 or greater. d is a number of about 5000 or less, more preferably about 2000 or less, and most preferably about 500 or less.

In a preferred embodiment, the acrylate and methacrylate ester reactive groups on the aryl moieties at the terminal 2- and 7- or 7'-position (terminal position) preferably correspond to Formula 3.

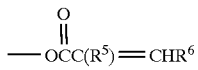

(3)

Preferably, $R^5$ is hydrogen or $C_{1-4}$ alkyl and more preferably hydrogen or methyl. $R^6$ is preferably hydrogen, $C_{1-20}$ hydrocarbyl or $C_{1-20}$ hydrocarbyloxy. More preferably, $R^6$ is hydrogen or $C_{1-20}$ hydrocarbyl. Even more preferably, $R^6$ is hydrogen, $C_{1-10}$ alkyl or $C_{6-10}$ aryl or alkyl-substituted aryl. Even more preferably, $R^6$ is hydrogen, $C_{1-4}$ alkyl or phenyl. Most preferably, $R^6$ is hydrogen.

In a preferred embodiment, the ethenyl moiety on the aryl at the terminal position corresponds to Formula 4,

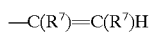

(4)

wherein:

$R^7$ is independently in each occurrence hydrogen, $C_{1-20}$ hydrocarbyl or $C_{1-20}$ hydrocarbyloxy. Preferably, $R^7$ is hydrogen, $C_{1-10}$ alkyl, $C_{6-10}$ aryl or alkyl-substituted aryl or $C_{1-20}$ alkoxy. Preferably, $R^7$ is hydrogen, $C_{1-4}$ alkyl, phenyl or $C_{1-4}$ alkoxy.

In one embodiment, the aryl moiety at the terminal position is a benzocyclobutene moiety which preferably corresponds to Formula 5,

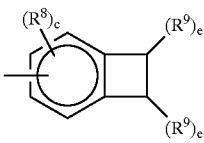

(5)

wherein:

$R^8$ is preferably $C_{1-20}$ alkyl, $C_{1-20}$ alkoxy, $C_{1-20}$ alkylthio $C_{6-20}$ aryl, $C_{6-20}$ aryloxy, $C_{6-20}$ arylthio, $C_{7-20}$ aralkoxy, $C_{7-20}$ alkaryloxy, $C_{7-20}$ alkarylthio, $C_{7-20}$ aralkyl, $C_{7-20}$ aralkoxy, $C_{7-20}$ aralkylthio, cyano, carboxylate, $C_{1-20}$ hydrocarbylcarbonyloxy, $C_{1-20}$ hydrocarbylsulfonyl, $C_{1-20}$ hydrocarbylsulfinyl or $C_{1-20}$ dialkylamino. $R^8$ is more preferably $C_{1-20}$ alkyl or cyano. Most preferably, $R^8$ is $C_{1-3}$ alkyl or cyano. $R^9$ is preferably cyano, carboxylate, $C_{1-20}$ hydrocarbylcarbonyloxy, nitro, halo, $C_{1-20}$ hydrocarbylsulfonyl, $C_{1-20}$ hydrocarbylsulfinyl, $C_{1-20}$ alkyl, amido or $C_{1-20}$ hydrocarbyloxy. $R^9$ is more preferably $C_{1-20}$ hydrocarbyloxy or cyano. c is an integer of about 0 to about 3. Preferably, c is from about 0 to about 1 and most preferably 0. e is an integer of from about 0 to about 2, preferably from about 0 to about 1 and most preferably about 0.

As used herein 2,7-aryl-9-substituted fluorenes refer to compounds where d is 1 and either of m or n is 1 and the other is 0.

In one preferred embodiment, the invention comprises 2,7-aryl-9,9-dihydrocarbyl- or cyclohydrocarbdiylfluorenes and 9,9-dihydrocarbyl- or cyclohydrocarbdiylfluorene oligomers and polymers which correspond to Formula 6,

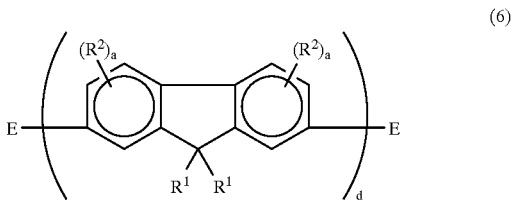

(6)

wherein E, $R^1$, $R^2$, a, and d are as described hereinbefore.

In another embodiment, the invention comprises 2,7-aryl-9-hydrocarbylidenylfluorenes and 9-hydrocarbylidenyl-fluorene oligomers and polymers thereof which preferably correspond to Formula 7,

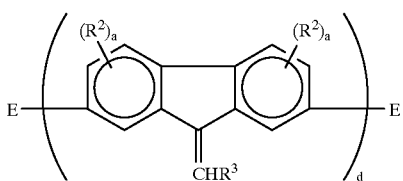

wherein E, $R^2$, $R^3$, a and d are as described hereinbefore.

In one preferred embodiment, the 2,7-aryl-9-hydrocarbylidenylfluorenes and 9-hydrocarbylidenylfluorene oligomers and polymers are 2,7-aryl-9-benzylidenylfluorenes and 9-benzylidenylfluorene oligomers and polymers which correspond to Formula 8,

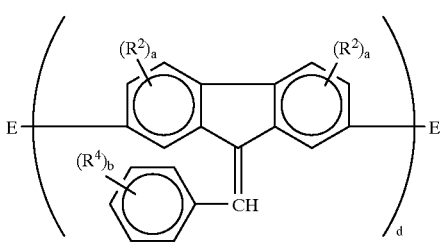

wherein E, $R^2$, $R^4$, a, b and d are as described hereinbefore.

As used herein, 2,7-aryl-9-substituted fluorenes refer to compounds corresponding to Formulas 6, 7 or 8 where d is 1. As used herein, 9-substituted fluorene oligomers and polymers correspond to Formulas 6, 7 or 8 wherein d is greater than 1 and Formulas 1 and 2 where both m and n are 1 or greater.

The fluorenes and fluorene oligomers or polymers of the invention demonstrate strong photoluminescence in dilute solutions or in the solid state. When such materials are exposed to a light of a wavelength of about 300 to about 700 nanometers, the materials emit light of wavelengths in the region of about 400 to about 800 nanometers. More preferably, such materials absorb light of wavelengths of from about 350 to about 400 nanometers and emit light of wavelengths in the region of about 400 to about 650 nanometers. The fluorenes and fluorene oligomers or polymers of the invention are readily soluble in common organic solvents. They are processable into thin films or coatings by conventional techniques. Upon curing, such films demonstrate resistance to common organic solvents and high heat resistance. Generally, the fluorene oligomers and polymers are liquid crystalline in nature. The fluorenes and fluorene oligomers or polymers of the invention are capable of crosslinking to form solvent resistant, heat resistant films at about 100° C. or more, more preferably at about 150° C. or more. Preferably, such crosslinking occurs at about 350° C. or less, more preferably about 300° C. or less and most preferably about 250° C. or less. The fluorenes and fluorene oligomers or polymers of the invention are stable at about 100° C. or more and more preferably about 150° C. or more. Stable, as used herein, means that such monomers or oligomers do not undergo crosslinking or polymerization reactions at or below the stated temperatures.

The fluorene oligomers or polymers of this invention preferably have a weight average molecular weight of about 1000 Daltons or greater, more preferably about 5000 Daltons or greater, even more preferably about 10,000 Daltons or greater, even more preferably about 15,000 Daltons or greater and most preferably about 20,000 Daltons or greater; preferably about 1,000,000 Daltons or less, more preferably about 500,000 Daltons or less and most preferably about 100,000 Daltons or less. Molecular weights are determined according to gel permeation chromatography using polystyrene standards.

Preferably, the 9-substituted fluorene oligomers or polymers demonstrate a polydispersity (Mw/Mn) of 5 or less, more preferably 4 or less, even more preferably 3 or less, even more preferably 2.5 or less and most preferably 2.0 or less.

The 2,7-aryl-9-substituted fluorenes and 9-substituted fluorene oligomers and polymers are prepared by contacting one or more 2,7-dihalo-9-substituted fluorenes with a haloaromatic compound in the presence of a nickel (zero valent) catalyst. The 9-substituted fluorene oligomers and polymers terminated at the terminal 2- and 7'-positions with hydrogen or a halogen are prepared by the process described above in the absence of a haloaromatic compound. The nickel (zero valent) catalyst is prepared in situ by contacting a divalent nickel salt with a reducing agent in the presence of a material capable of acting as a ligand and optionally a material capable of accelerating the reactions.

The 2,7-dihalo-9-substituted fluorenes may optionally be substituted at the 3-, 4-, 5- and/or 6-position with a substituent which does not interfere with the processes described hereinafter. Preferably, such substituents are materials which do not contain active hydrogen moieties. Preferably, the 2,7-dihalo-9-substituted fluorene corresponds to Formulas 9 or 10,

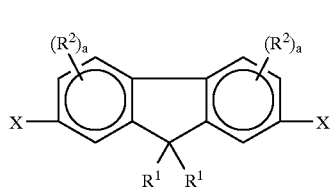

or

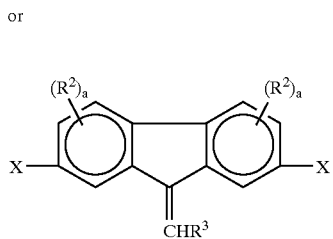

wherein $R^1$, $R^2$, $R^3$ and a are as previously defined and X is a halogen moiety. In Formulas 9 and 10, X is preferably bromine or chlorine.

The 2,7-dihalo-9-substituted fluorenes and 2,7-dihalo-9-hydrocarbylidenylfluorenes are prepared from 2,7-dihalofluorene, which is commercially available, by the processes described hereinafter.

The haloaromatic compound used to prepare the 2,7-aryl-9-substituted fluorenes and 9-substituted fluorene oligomers and polymers comprises an aromatic compound substituted on the ring with a halogen and may further be substituted with a moiety capable of crosslinking or chain extension. Preferably, such compound corresponds to Formula 11, $$X\text{—}F \qquad (11)$$

wherein X is as previously defined and F is an aryl moiety or an aryl moiety substituted with a moiety capable of crosslinking or chain extension or a trialkylsiloxy moiety.

Preferably, the haloaromatic compound corresponds to Formulas 12 or 13,

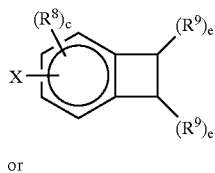

(12)

or

(13)

wherein

Z is a trialkylsiloxy, glycidyl ether, acrylate ester, methacrylate ester, ethenyl, ethynyl, maleimide or a trifluorovinyl ether moiety. Preferably, Z is a trialkylsiloxy moiety, ethenyl, ethynyl, maleimide or trifluorovinyl ether moiety. More preferably, Z is a trialkylsiloxy moiety.

In one preferred embodiment, the haloaromatic compound is a halogen-substituted benzocyclobutene moiety according to Formula 12.

The preparation of the 2,7-diaryl-9-substituted fluorenes and the 9-substituted fluorene oligomers or polymers may be illustrated by Equations 1 and 2.

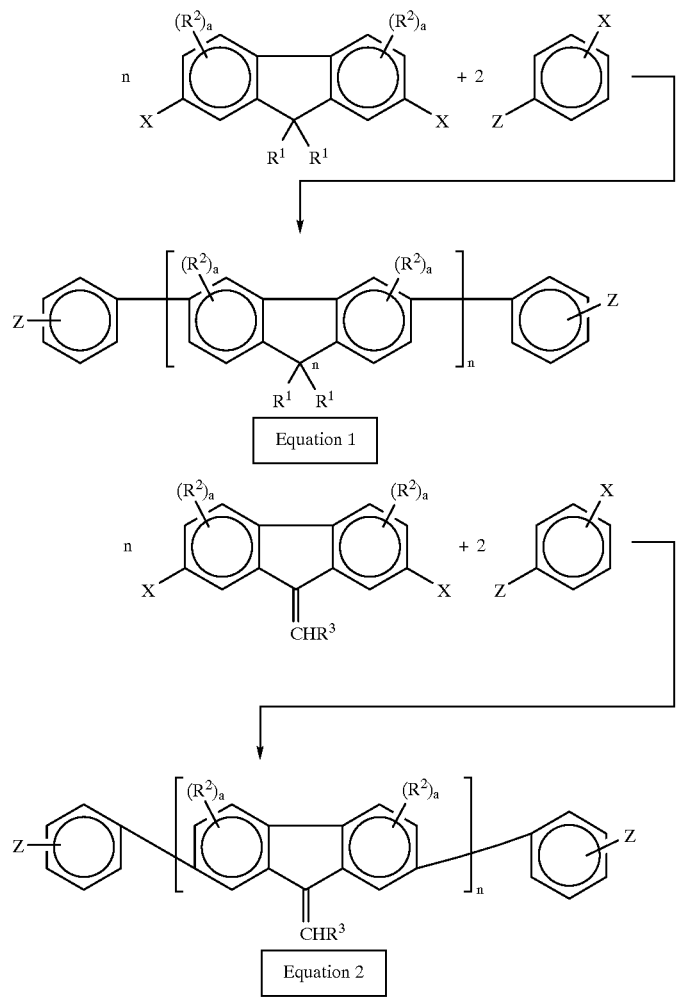

The 2,7-dihalo-9-substituted fluorene and haloaromatic compound may be contacted in a wide range of ratios, depending upon the desired degree of oligomerization or polymerization. Preferably, the mole ratio of 2,7-dihalo-9-substituted fluorene to haloaromatic compound is about 1:2 or greater, preferably about 1:1 or greater and more preferably about 2:1 or greater. Preferably, the ratio is about 50:1 or less, and more preferably about 25:1 or less.

In the embodiment wherein it is desired to prepare a 2,7-diaryl-9-substituted fluorene (where d is 1), the mole ratio of 2,7-dihalo-9-substituted fluorene to haloaromatic compound is about 1:2. In the embodiment where oligomers or polymers are desired (where d is greater than 1), a greater ratio of 2,7-dihalo-9-substituted fluorene is used relative to the haloaromatic compound. Higher ratios facilitate the preparation of higher molecular weight oligomers and polymers.

In a preferred embodiment, the reaction of the 2,7-dihalo-9-substituted fluorene with haloaromatic compound takes place according to the procedures of Colon et al., described in *Journal of Polymer Science*, Part A, Polymer Chemistry Edition, Vol. 28, p. 367 (1990), incorporated herein by reference, and Colon et al., *Journal of Organic Chemistry*, Vol. 51, p. 2627 (1986), relevant parts incorporated herein by reference.

The reactants are contacted in a polar solvent, preferably dimethylformamide, N,N-dimethylacetamide or N-methylpyrrolidinone. Up to about 50 volume percent of a non-amide co-solvent can be used. Preferable co-solvents are aromatic hydrocarbons and ethers, for instance, tetrahydrofuran. The process is preferably conducted in the absence of oxygen and moisture, as the presence of oxygen is detrimental to the catalyst and the presence of a significant amount of water leads to premature termination of the process. More preferably, the reaction is performed under an inert atmosphere such as nitrogen or argon.

The catalyst is formed from a divalent nickel salt. The nickel salt may be any nickel salt which can be converted to the zero valent state under reaction conditions. Preferable nickel salts are the nickel halides, with nickel chloride and nickel bromide most preferred. The divalent nickel salt is present in an amount of about 0.01 mole percent or greater, more preferably about 0.1 mole percent or greater and most preferably about 1.0 mole percent or greater based on the amount of haloaromatic compound and 2,7-dihalofluorene present. The amount of divalent nickel salt present is preferably about 30 mole percent or less, more preferably about 15 mole percent or less based on the amount of haloaromatic compound and 2,7-dihalofluorene present.

The reaction is performed in the presence of a material capable of reducing the divalent nickel ion to the zero valent state. Suitable material includes any metal which is more easily oxidized than nickel. Preferable metals include zinc, magnesium, calcium and lithium. The preferred reducing agent is zinc in the powder form. At least stoichiometric amounts of reducing agent based on haloaromatic compounds are required to maintain the nickel species in the zero valent state throughout the reaction. Preferably, about 150 mole percent or greater, more preferably about 200 mole percent or greater, and most preferably about 250 mole percent or greater based on the haloaromatic compound and 2,7-dihalofluorene is used. More preferably, the reducing agent is present in an amount of about 500 mole percent or less, more preferably about 400 mole percent or less and most preferably about 300 mole percent or less based on the amount of haloaromatic compound and 2,7-dihalofluorene.

The process is performed in the presence of a material capable of acting as a ligand. Preferred ligands include trihydrocarbylphosphines. More preferred ligands are triaryl or trialkylphosphines with triphenylphosphines being the most preferred. The compound capable of acting as a ligand is present in an amount of from about 10 mole percent or greater, more preferably about 20 mole percent or greater based on the haloaromatic compound and 2,7-dihalofluorene. The compound capable of acting as a ligand is preferably present in an amount of about 100 mole percent or less, more preferably about 50 mole percent or less and most preferably about 40 mole percent or less based on the amount of haloaromatic compound and 2,7-dihalofluorene.

The reaction is performed in the presence of a compound capable of accelerating the reaction. Such accelerator comprises 2,2'-bipyridine or an alkali metal halide. Preferred alkali metal halides useful as accelerators include sodium bromide, potassium bromide, sodium iodide and potassium iodide. The most preferred accelerator is 2,2'-bipyridine. The accelerator is used in a sufficient amount to accelerate the reaction. Preferably, the accelerating compound is used in amount of about 0.1 mole percent or greater, preferably about 0.5 mole percent or greater and most preferably about 1.0 mole percent or greater based on the haloaromatic compound and 2,7-dihalofluorene. Preferably, the accelerating compound is present in an amount of about 100 mole percent or less, more preferably about 50 mole percent or less and most preferably about 5 mole percent or less based on the amount of haloaromatic compound and 2,7-dihalofluorene.

The reaction can be performed at any temperature at which the reaction proceeds at a reasonable rate. Preferably, the reaction is performed at a temperature of about 25° C. or greater, more preferably about 50° C. or greater and most preferably about 70° C. or greater. Below about 25° C., the rate of reaction is unacceptably low. Preferably, the reaction is performed at a temperature of about 200° C. or less, more preferably about 150° C. or less and most preferably about 125° C. or less. Temperatures substantially higher than about 200° C. can lead to degradation of the catalyst. The reaction time is dependent upon the reaction temperature, the amount of catalyst and the concentration of the reactants. Reaction times are preferably about 1 hour or greater and more preferably about 10 hours or greater. Reaction times are about 100 hours or less, more preferably about 72 hours or less and most preferably about 48 hours or less. The amount of solvent used in this process can vary over a wide range. Generally, it is desired to use as little solvent as possible. Preferably, about 10 liters of solvent per mole of 2,7-dihalo-9-substituted fluorene or less is used, more preferably about 5 liters or less is used, and most preferably about 2 liters or less is used. The lower limit on amount of solvent used is determined by practicality, that is, handleability of the solution and solubility of the reactants in the solvent. The resulting 2,7-diaryl-9-substituted fluorenes and 9-substituted fluorene oligomers and polymers are recovered according to conventional techniques; preferred techniques include filtration and precipitation using a nonsolvent. Alternatively, in another embodiment, the 2,7-diaryl-9-substituted fluorenes and 9-substituted fluorene oligomers and polymers may be prepared by a process disclosed in Ioyda et al., *Bulletin of the Chemical Society of Japan*, Vol. 63, p. 80 (1990), relevant parts incorporated herein by reference. Such method is similar to the method described hereinbefore. In particular, the catalyst is a divalent nickel salt introduced as a nickel halide bis-triphenylphosphine complex. The reaction may be performed in a variety of solvents including acetone, dimethylformamide, tetrahydrofuran and acetonitrile. The reaction is accelerated by the addition of about 10 mole percent of an organo-soluble iodide such as tetraethylammonium iodide. Such a reaction is performed at a temperature of from about 20° C. to about 100° C. for about 1 to about 24 hours.

In another embodiment, the subject compounds of the invention may be prepared via the processes disclosed by Yamamoto, *Progress in Polymer Science*, Vol. 17, p. 1153

(1992), relevant parts incorporated herein by reference. In such process, 2,7-dihalo-9-substituted fluorene monomers are contacted with at least a stoichiometric amount of nickel catalyst in the form of nickel(1,5-cyclooctadiene) complex and at least a stoichiometric amount of 1,5-cyclooctadiene as a ligand in an inert solvent, such as tetrahydrofuran. The reaction is preferably conducted at about 70° C. or higher for about 2 or more days. In another embodiment, the subject compounds of the invention may be prepared by the process disclosed in Miyaura et al., *Synthetic Communication*, Vol. 11, p. 513 (1981) and Wallow et al., *American Chemical Society Polymer Preprint* Vol. 34, (1), p. 1009 (1993), relevant parts of both references incorporated herein by reference. In such process, 2,7-dihalo-9-substituted fluorenes are converted to the corresponding diboronic acid by reacting the 2,7-dilithio- or 2,7-diGrignard-9-substituted fluorenes with trialkyl borates. M. Rehalin et al., as disclosed in *Makromoleculaire Chemie*, Vol. 191, pp. 1991–2003 (1990), relevant parts incorporated herein by reference. The diboronic acid is then reacted with a 2,7-dihaloflourene in the presence of a catalytic amount of tetrakistriphenylphosphine palladium and an aqueous base at about 70° C. or higher for about 10 to about 100 hours in an inert solvent, for instance toluene, ethanol and the like.

In the embodiment wherein the reactive moiety on the aryl moieties of the 2,7-aryl-9-substituted fluorene or 2,7'-aryl-9-substituted fluorene oligomers and polymers are trialkylsiloxy moieties, the trialkylsiloxy moieties may be converted to hydroxy moieties by contact with concentrated acid, such as hydrochloric acid, in an organic solvent.

A halophenyltrialkylsiloxy ether is reacted with the 2,7-dihalo-9-substituted fluorene to prepare an oligomer having end-groups comprising phenyltrialkylsiloxy moieties using the same process as used to react a haloaromatic compound with a 2,7-dihalo-9-substituted fluorene. This reaction sequence is illustrated by Equation 3 wherein $R^{10}$ is a $C_{1-20}$ alkyl moiety, preferably a $C_{1-4}$ alkyl moiety. The trialkylsiloxy moieties can be converted to hydroxy moieties by refluxing the resulting product in tetrahydrofuran and concentrated hydrochloric acid. This reaction sequence is illustrated by Equation 4.

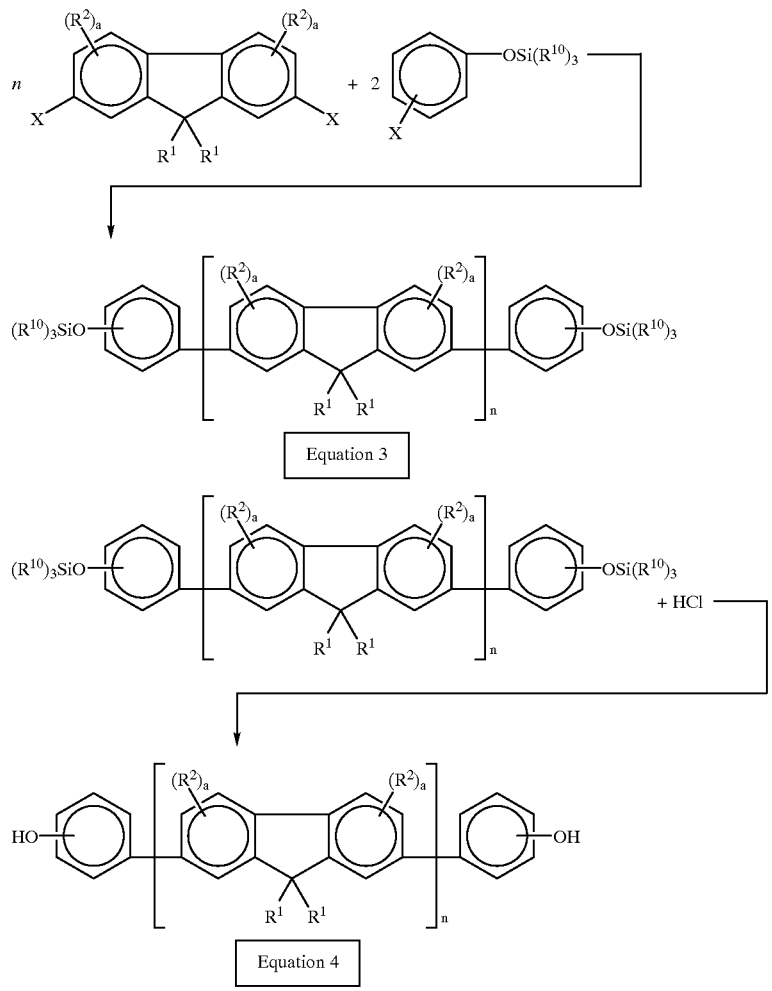

The hydroxy moieties of the 2,7'-aryl substituents may be converted to cyanate moieties by well-known cyanation reactions. See, for example, U.S. Pat. No. 4,478,270; Martin, *Organic Synthesis*, Vol. 61, p. 35; and *Handbook of Preparative Inorganic Chemistry*, p. 1,662 (1963), Academic Press, New York. The relevant teachings of these references are incorporated herein by reference. This reaction sequence is illustrated by Equation 5.

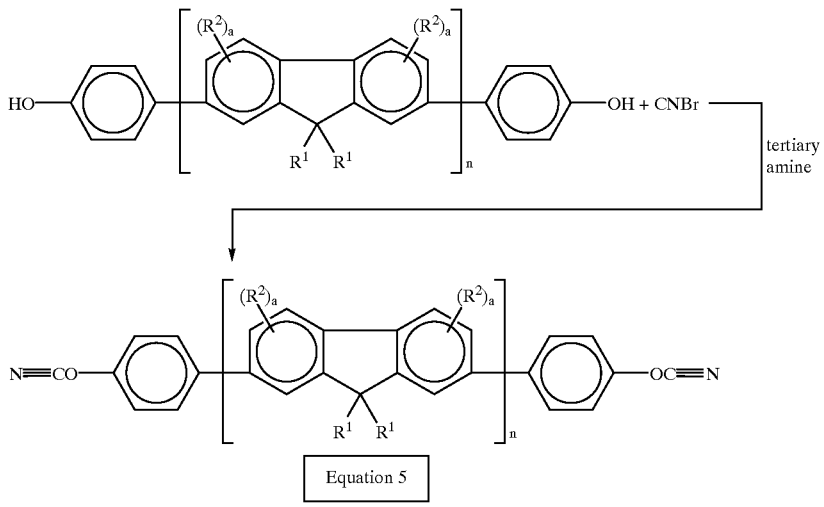

Equation 5

In one preferred embodiment, the 2,7-hydroxyaryl-9-substituted fluorene or 2,7'-hydroxyaryl-9-substituted fluorene oligomer or polymer is contacted with cyanogen halide dissolved in a chlorinated hydrocarbon or a secondary or tertiary alcohol, in the presence of a tertiary amine at a temperature of about 0° C. or less under conditions such that the hydroxy moieties are replaced with cyanate moieties. Preferably, the contacting occurs in the presence of a dilute base such as alkali or alkaline metal hydroxides, alkali or alkaline metal carbonates, alkali or alkaline metal bicarbonates or tertiary amines. Preferred bases are the tertiary amines with the aliphatic tertiary amines being most preferred. This process is preferably run at a temperature of about 0° C. or lower with temperatures of about −10° C. or lower being most preferred. It is preferable to perform such process under an inert gas atmosphere. The cyanated 2,7-aryl-9-substituted fluorenes or 2,7'-aryl-9-substituted fluorene oligomers or polymers may be recovered by washing the reaction solution with a dilute base to remove excess cyanogen chloride. The reaction solution is thereafter washed with water so as to remove any salt prepared from the hydrochloride by-product and base. The reaction solution is then contacted with the dilute acid to neutralize any base which may be present. Thereafter, the reaction solution is contacted with water again so as to remove any other impurities and the cyanated 2,7-aryl-substituted-9-substituted fluorenes and 2,7'-aryl-9-substituted fluorene oligomers or polymers are recovered by drying the solution with the use of a dessicant.

The reactions illustrated by Equations 3, 4 and 5 can also be performed starting with 9-hydrocarbylidenyl-2,7-dihalofluorene.

In another embodiment, the hydroxy moieties of the 2,7-hydroxyaryl-9-substituted fluorene or 2,7'-hydroxyaryl-9-substituted fluorene oligomer or polymer may be converted to glycidyl ether moieties by processes well known in the art. Such glycidyl ethers are preferably prepared by contacting the 2,7-hydroxyaryl-9-substituted fluorene or 2,7'-hydroxyaryl-9-substituted fluorene oligomer or polymer with epihalohydrin under conditions to form aryl moieties with chlorohydrin groups at their termini. The chlorohydrin groups are dehydrohalogenated to form an epoxy or glycidyl ring by contacting them with sodium hydroxide. Such process is described in *Handbook of Epoxy Resins,* Lee and Neville (1967), relevant parts incorporated herein. This process is illustrated by Equation 6.

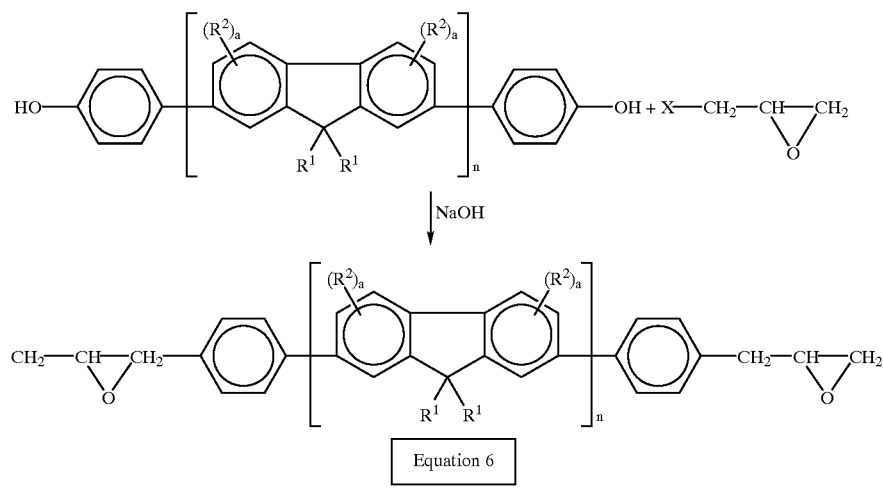

Equation 6

2,7-Dihalo-9,9-dihydrocarbylfluorenes or 2,7-dihalo-9,9-cyclohydrocarbdiylfluorenes are prepared by the reaction of a 2,7-dihalofluorene with at least about 2 equivalents of hydrocarbyl halide or hydrocarbyl dihalide in the presence of a phase transfer catalyst and an alkali metal hydroxide. The hydrocarbyl halides preferably correspond to the formula $R^1X$ and the hydrocarbyl dihalides preferably correspond to the formula $XR^1X$ wherein $R^1$ and X are as defined hereinbefore. The hydrocarbyl halide, or hydrocarbyl dihalide is contacted with the 2,7-dihalofluorene in an equivalent ratio such that a high yield of 2,7-halo-9,9-dihydrocarbylfluorene or 2,7-dihalo-9,9-cyclohydrocarbdiylfluorene is prepared. Preferably, the equivalent ratio of hydrocarbyl halide or hydrocarbyl dihalide to 2,7-dihalofluorene is about 2:1 or greater, more preferably about 2.2:1 or greater and even more preferably about 3:1 or greater. Preferably, the equivalent ratio of hydrocarbyl halide or dihydrocarbyl dihalide to 2,7-dihalofluorene is about 6:1 or less, more preferably about 5:1 or less and most preferably about 4:1 or less.

The process to prepare 2,7-dihalo-9,9-dihydrocarbyl- or 9,9-cyclohydrocarbdiylfluorenes is performed in the presence of an alkali metal hydroxide in sufficient amount to facilitate the efficient reaction of the hydrocarbyl halide or dihydrocarbyl dihalide with the 2,7-dihalofluorene. Preferably, about 2 equivalents or greater of alkali metal hydroxide are used in relation to 2,7-dihalofluorene and more preferably at least about 3 equivalents of alkali metal hydroxide per equivalent of 2,7-dihalofluorene. Preferably, about 20 equivalents or less of alkali metal hydroxide per equivalent of 2,7-dihalofluorene are used, more preferably about 8 equivalents or less and most preferably about 4 equivalents or less. Preferred alkali metal hydroxides useful are sodium hydroxide and potassium hydroxide, with sodium hydroxide being most preferred.

The process to prepare 2,7-dihalo-9,9-dihydrocarbyl- or 9,9-cyclohydrocarbdiylfluorenes is an interfacial process using phase transfer catalysts. Any phase transfer catalyst known to those skilled in the art may be used in this process. A sufficient amount of such phase transfer catalyst is used to facilitate the reaction of the hydrocarbyl halides or hydrocarbyl dihalides with the 2,7-dihalofluorenes in a reasonably efficient manner. Preferable phase transfer catalysts include quaternary ammonium salts, quaternary phosphonium salts, polyethylene glycols and crown ethers. More preferred phase transfer catalysts are the quaternary ammonium salts.

The phase transfer catalysts are used preferably in an amount of about 0.0001 mole or greater of catalyst per mole of 2,7-dihalofluorene, more preferably about 0.001 mole or greater and even more preferably about 0.01 mole or greater. Preferably, about 0.2 mole or less of catalyst per mole of 2,7-dihalofluorene is used, more preferably about 0.15 mole or less and even more preferably about 0.01 mole or less may be used.

This process may be performed neat or in solvent. Water and common organic solvents are preferred solvents. Among more preferred solvents are polar organic solvents, chlorinated hydrocarbons and aromatic hydrocarbons. Among even more preferred solvents are dimethylsulfoxide, dimethylformamide, water, methylene chloride, toluene and the like. A most preferred solvent is dimethylsulfoxide.

The process may be performed under subatmospheric, atmospheric or superatmospheric pressures. It is preferred to perform the process at atmospheric pressure, as it is the most cost-efficient method. The process may be performed at any temperature at which the reaction proceeds at a reasonable rate. The reaction is exothermic, although in some instances, external heating may be advantageous to accelerate the rate of reaction. Preferably, the process is performed at a temperature of about 0° C. or greater, more preferably about 20° C. or greater and most preferably about 25° C. or greater. The process is preferably performed at a temperature of about 100° C. or less, more preferably about 80° C. or less and most preferably about 70° C. or less.

The resulting 2,7-dihalo-9,9-dihydrocarbyl- or 9,9-cyclohydrocarbdiylfluorenes may be recovered by conventional means. Among preferred means for recovering such compounds are filtration of solid products and extraction of liquid products with water-immiscible organic solvents. Among more preferred water-immiscible organic solvents useful for extraction are diethyl ether, hexane, chloroform and methylene chloride.

In another embodiment, 9-substituted 2,7-dihalofluorenes are prepared by the reaction of a hydrocarbylaldehyde or a substituted hydrocarbylaldehyde in the presence of base as a catalyst. Preferably, the aldehyde corresponds to the formula

wherein $R^3$ is defined hereinbefore. In a more preferred embodiment, the hydrocarbyl moiety is a phenyl, substituted phenyl, $C_{3-10}$ aliphatic or $C_{5-10}$ cycloaliphatic and the aldehyde is benzaldehyde, substituted benzaldehyde, $C_{3-10}$ aliphatic aldehyde or $C_{5-10}$ cycloaliphatic aldehyde. The 2,7-dihalofluorene is reacted with a sufficient amount of hydrocarbylaldehyde to prepare the 2,7-dihalo-9-hydrocarbylidenyl-substituted fluorenes in high yield. Preferably, the ratio of hydrocarbylaldehyde to 2,7-dihalofluorene is about 1.0 or greater, more preferably about 1.5 or greater and even more preferably about 2 or greater. Preferably, the mole ratio of hydrocarbylaldehyde to 2,7-dihalofluorene is about 6 or less and more preferably about 3 or less. The reaction is performed using a base as a catalyst. Preferable bases useful as catalysts for this reaction are tertiary ammonium hydroxides such as benzyltrialkylammonium hydroxide and tetraalkylammonium hydroxides. More preferred bases useful as catalysts in this reaction are benzyltrimethylammonium hydroxide, tetraethylammonium hydroxide and tetrabutylammonium hydroxide. The base is present in an amount based on the amount of 2,7-dihalofluorene of about 10 weight percent or greater, more preferably about 20 weight percent or greater and most preferably about 25 weight percent or greater; preferably about 50 weight percent or less, more preferably about 40 weight percent or less and most preferably about 30 weight percent or less.

This process may be performed at a temperature at which a reasonable rate of reaction occurs. Preferably, the reaction is performed at a temperature of about 0° C. or greater, more preferably about 10° C. or greater and most preferably about 15° C. or greater. Preferably, the reaction is performed at a temperature of about 50° C. or less, more preferably about 40° C. or less and most preferably about 30° C. or less.

The process is preferably performed in a solvent. Preferred solvents are polar organic solvents. Preferred polar organic solvents are pyridine, picolines, collidines, methanol, ethanol, acetonitrile, tetrahydrofuran and dimethylformamide. More preferably, the reaction is performed in pyridine or picolines. The concentration of the reactants in the solvent is preferably about 5 percent or greater, more preferably about 10 percent or greater and most preferably about 15 percent or greater. The concentration of the reactants in the solvent is preferably about 50 percent by weight or less, more preferably about 40 percent by weight or less and most preferably about 20 percent by weight or less.

The reaction may be performed at ambient, superatmospheric and subatmospheric pressures. The reaction is preferably performed in the absence of oxygen, more preferably in an inert atmosphere such as in nitrogen or argon.

The 2,7-dihalo-9,9-bis-$C_{4-16}$-hydrocarbyl carbonyloxy-substituted fluorenes may be prepared by base-catalyzed addition of 2,7-dihalofluorene to alkyl acrylates and alkyl methacrylates as described in U.S. Pat. No. 3,641,115, relevant parts incorporated herein by reference.

The $C_{9-16}$ aryl(trialkylsiloxy)-substituted 2,7-dihalofluorenes may be prepared by the following process. 2,7-dihalofluorenone is reacted with phenol in a mixture of methanesulfonic acid and 3-mercaptopropionic acid to provide 9,9-bis(4-hydroxyphenyl)2,7-dihalofluorene which is then treated with a trialkylsilyl chloride in the presence of a base to yield the trialkylsiloxy-9,9-bis(4-trialkylsiloxy-phenyl)-2,7-dihalofluorene. 2,7-dihalofluorenone can be prepared by the oxidation of 2,7-dihalofluorene with oxygen in the presence of a base, such as potassium t-butoxide, in t-butyl alcohol. The conditions for this process are disclosed in Yang, "Novel Carbon Catalysts: Oxidation in Basis Solution," *J. Organic Chemistry*, Vol. 58, p. 3754 (1958), incorporated herein by reference. Alternatively, 2,7-dihalofluorene can be oxidized to 2,7-dihalofluorenone by contacting it with chromium oxide ($CrO_3$) in acetic acid according to the process disclosed in Hodgkinson et al., *J. Chem. Soc.*, Vol. 43, pp. 163–172 (1983), relevant parts incorporated by reference. The 2,7-dihalofluorenone is contacted with about 3 to about 10 equivalents of phenol in the presence of from about 30 to about 100 percent by weight of methanesulfonic acid and from about 2 to about 10 percent by weight of mercaptopropionic acid. The reaction is preferably performed at a temperature of from about 20° C. to about 50° C. The 4-hydroxyphenyl-dihalofluorene is recovered by conventional techniques before reaction with the trialkylsilyl chloride.

The 2,7-dihalo-9,9-bis(4-hydroxyphenyl)fluorene is contacted with from about 2.2 to about 3.0 equivalents of trialkylsilyl chloride in the presence of from about 3.0 to about 6.0 equivalents of base. The reaction is preferably performed at a temperature of from about 20° C. to about 40° C. The reaction is performed in a solvent of dimethylformamide, dimethylacetamide, and the like. Imidazole is the preferred base for use in the process. The 2,7-dihalo-9,9-bis(4-trialkylsiloxy)fluorene can be recovered by conventional techniques.

The 2,7-dihalo-9,9-disubstituted fluorenes may be further substituted on the 3-, 4-, 5- and/or 6-position by a variety of synthesis techniques. Preferably, the 3-, 4-, 5- and/or 6-positions are substituted prior to substitution at the 9-position. In many instances, the reaction sequence to place substituents at the 3-, 4-, 5- and/or 6-position may result in unwanted substitution on the substituents at the 9-position if the substitution is performed after the 9-position substitution. Unless otherwise stated in the discussions hereinafter, the synthetic sequences described relate to substitution at the 3-, 4-, 5- and/or 6-positions prior to substitution at the 9-position. Those instances where the 9-position can be substituted prior to performing a specific reaction sequence will be noted.

Hydroxy or alkoxy groups may be substituted in such positions by, in a first step, a Friedel-Crafts acylation of 2,7-dihalofluorene with acetyl chloride and aluminum chloride to prepare a diketone derivative. See *Advanced Organic Chemistry*, "Reactions, Mechanisms and Structures," Third Edition, Jerry March, John Wiley & Sons, p. 484 (1985), relevant parts incorporated herein by reference. In this embodiment, the starting fluorene may be unsubstituted or substituted at the 9-position with two $C_{1-20}$ alkyl moieties. Where the fluorene is unsubstituted at the 9-position, the product of this reaction sequence is subjected to the previously described reaction sequences to substitute the fluorene at the 9-position.

The 2,7-dihalo-9,9-dialkylfluorene or 2,7-dihalofluorene is added in an organic solvent, preferably tetrachloroethane or dichloromethane, to a mixture of aluminum chloride and acetyl chloride in the same organic solvent. A small excess of acetyl chloride, about 10 mole percent based on the 2,7-dihalofluorene, is typically used. The amount of aluminum chloride used is from about 2 to about 3 equivalents based on the 2,7-dihalofluorene. The reaction mixture may be optionally heated to a temperature as high as about 100° C. for a period of time to effect acetylation. The resulting product can thereafter be oxidized with a peracid to prepare diester derivatives via the well-known Baeyer-Villiger oxidation. See March, supra, pp. 990–991, relevant parts incorporated herein by reference. The oxidation agent is preferably a peracid and more preferably peracetic acid, trifluoroperacetic acid, perbenzoic acid or m-chloroperbenzoic acid. The oxidizing agent is used in stoichiometric amount or in a small excess, up to about 5 mole percent based on the 2,7-dihalofluorene. Reaction solvent may be any solvent not oxidizable by the oxidation agent; among preferred solvents are chloroform, dichloromethane and ethyl acetate. The reaction temperature may range from about 0° C. to about 70° C. and reaction time may range from about 1 to about 5 hours.

Hydroxy substituents at the 3-, 4-, 5- and/or 6-positions may be prepared by hydrolysis of the ester-substituted derivative. Hydrolysis of the esters of the dihalofluorene and 2,7-dihalo-9,9-dialkylfluorene may be effected by refluxing the esters for about 1 to about 10 hours in a solvent with an alkali metal hydroxide, preferably sodium hydroxide or potassium hydroxide, followed by acidification of the resulting phenolates to the desired phenols. A suitable solvent is any solvent which dissolves the esters and base and is not attacked by the base. Preferable solvents are water, lower alcohols (e.g., methanol, ethanol and isopropyl alcohol), tetrahydrofuran, dioxane or mixtures thereof. From about 2 to about 8 equivalents of base are used based on the amount of the fluorene present. Thereafter, the reaction mixture is contacted with an acid to form the phenol. Preferable acids include dilute nitric, hydrochloric and sulfuric acid. The acid is used in an amount of from about 2 to about 4 equivalents. To effect acid catalyzed hydrolysis, the acid is contacted with the esters in the same solvent as used for contacting the esters with the base. This contacting occurs at a temperature of from about 20° C. to about 100° C. over a time period of about 1 to about 24 hours.

The hydroxy-substituted 2,7-dihalo-9,9-dialkylfluorenes or hydroxy-substituted 2,7-dihalofluorenes may be alkylated by reaction with alkyl halides to prepare alkoxy-substituted 2,7-dihalo-9,9-dialkylfluorenes or alkoxy-substituted 2,7-dihalofluorenes. The method for such alkylation is similar to that described above.

In yet another embodiment, a hydroxy-substituted 2,7-dihalofluorene or 2,7-dihalo-9-dialkyl hydroxy-substituted fluorene may be arylated by reaction with an aryl iodide catalyzed by copper. The reaction is conducted by boiling a mixture of an aryl iodide, a phenol, a base and copper bronze in a high boiling solvent for about 5 to about 50 hours. The aryl iodide and base are typically used in excess of about 50 percent by weight or greater based on the amount of the fluorene present. The addition of a small amount of a crown ether can be used to facilitate a faster reaction. A preferred base is potassium carbonate. Preferable high boiling solvents include aromatic hydrocarbons, chlorinated aromatic hydrocarbons and aromatic hydrocarbons containing nitrogen in the aromatic ring. More preferred solvents include quinoline, pyridine, chlorobenzene and 1,2-dichlorobenzene.

The 2,7-dihalo-9-substituted fluorenes may be substituted at the 3-, 4-, 5- and/or 6-positions with hydroxy, hydrocarbyloxy, cyano, thiocyano or thioaryl moieties. The methods of preparing such substituted materials are described hereinafter.

In one step, a 2,7-dihalofluorene or a 2,7-dihalo-9,9-dialkylfluorene, preferably 2,7-dichlorofluorene, is reacted with nitric acid and sulfuric acid under conditions such that one or more of the 3-, 4-, 5- and/or 6-positions is substituted with one or more nitro moieties. Nitration is typically effected by concentrated nitric acid, a mixture of concentrated nitric acid and concentrated sulfuric acid, or fuming nitric acid at about 0° C. to about 50° C. for about 1 to about 10 hours. A solvent which is not attacked by the nitrating agent may be used. Preferable solvents include carbon tetrachloride, acetic acid, acetic anhydride or mixtures thereof. The 2,7-dihalofluorene or 2,7-dihalo-9,9-dialkylfluorene is contacted with from about 2 to about 4 equivalents of nitric acid per equivalent of 2,7-dihalofluorene or 2,7-dihalo-9,9-dialkylfluorene. Sulfuric acid, if present, is present in an amount of from about 0.5 to about 2 equivalents per equivalent of 2,7-dihalofluorene or 2,7-dihalo-9,9-dialkylfluorene.

The nitro groups on the 2,7-dihalo- or 2,7-dihalo-9,9-dialkylfluorene may be reduced to amines by techniques well known in the art, for instance, dissolving metal reduction, catalytic hydrogenation, and the like. See March, supra, p. 1103, relevant parts incorporated herein by reference. Dissolving metal reduction of nitrated 2,7-dihalofluorene or 2,7-dihalo-9,9-dialkylfluorene to the corresponding amine derivatives may be effected by the various well-known combinations of metals (Zn, Fe, Sn, $SnCl_2$) and aqueous (neutral, acidic or basic) solutions as taught in *Organic Syntheses, Collective Volume II*, pp. 160, 175, 255, 448 and 501 (1943), relevant parts incorporated herein by reference. This reaction sequence can be performed before or after final substitution at the 9-position.

The amine-substituted, 2,7-dihalo-9-dialkylfluorenes or amine-substituted 2,7-dihalofluorenes can be converted to tertiary amines by alkylation with alkyl halides or by arylation with aryl iodides when catalyzed by copper. These conversions can be performed before or after final substitution at the 9-position. Arylation of aromatic amines is very similar to the Ullmann ether synthesis discussed above. Procedures for this conversion may be found in *Organic Syntheses, Collective Volume I*, p. 554 (1932), relevant parts incorporated herein by reference. An improved procedure using crown ether as a phase-transfer catalyst is disclosed by Gauthier and Frechet in *Synthesis*, p. 383 (1987), relevant parts incorporated herein by reference.

Alternatively, the diamine of 2,7-dihalofluorene or 2,7-dihalo-9,9-dialkylfluorene may be treated with nitrous acid to yield the diazonium salt. Displacement of the $N^{+2}$ moiety by nucleophilic agents, such as water, alcohol, cyanide, thiocyanate or thiophenate, results in formations of the corresponding phenol, ether, nitrile, thiocyanate or sulfite.

Diazotization of the amine-substituted 2,7-dihalofluorene or amine-substituted, 2,7-dihalo-9,9-dialkylfluorene may be effected by contacting an agitated mixture of the amine compound with cold aqueous sodium nitrate solution and concentrated HCl at about 0° C. Preferable solvents for the sodium nitrate solution are polar solvents, with dioxane and water being more preferred. Preferably, the concentration of sodium nitrate in the solution is from about 10 to about 50 percent by weight. The amount of concentrated HCl is from about 2 to about 4 equivalents per equivalent of amine-substituted 2,7-dihalofluorene or amine-substituted 2,7-dihalo-9,9-dialkylfluorene.

The 2,7-diaryl-9-substituted fluorenes and 9-substituted fluorene oligomers and polymers are useful in preparing coatings and films. Such coatings and films can be useful as emitting layers in polymeric light-emitting diodes, in protective coatings for electronic devices and as fluorescent coatings. The thickness of the coating or film is dependent upon the ultimate use. Generally, such thickness can be from about 0.01 to about 200 microns. In that embodiment wherein the coating is used as a fluorescent coating, the coating or film thickness is from about 50 to about 200 microns. In that embodiment where the coatings are used as electronic protective layers, the thickness of the coating can be from about 5 to about 20 microns. In that embodiment where the coatings are used in a polymeric light-emitting diode, the thickness of the layer formed is about 0.05 to about 2 microns. The compounds of the invention and their oligomers or polymers form good pinhole- and defect-free films. Such films can be prepared by means well known in the art including spin-coating, spray-coating, dip-coating and roller-coating. Such coatings are prepared by a process comprising applying a composition to a substrate and exposing the applied composition to conditions such that a film is formed. The conditions which form a film depend upon the application technique and the reactive end groups of the aryl moiety. In a preferred embodiment, the composition applied to the substrate comprises the 2,7-diaryl-9-substituted fluorene or 9-substituted fluorene oligomers or polymers dissolved in a common organic solvent. Preferred solvents are aliphatic hydrocarbons, chlorinated hydrocarbons, aromatic hydrocarbons, ketones, ethers and the like. It is preferable that such solvents have relatively low polarity. Preferably, the solution contains from about 0.5 to 10 weight percent of the 2,7-diaryl-9-substituted fluorene or 9-substituted fluorene oligomers or polymers. For thin coatings, it is preferred that the composition contains from about 0.5 to 5.0 percent by weight of the 2,7-diaryl-9-substituted fluorene or 9-substituted fluorene oligomers or polymers. This composition is then applied to the appropriate substrate by the desired method. The coating is then exposed to the necessary conditions to cure the film, if needed, to prepare a film having high solvent and heat resistance. The films are preferably substantially uniform in thickness and substantially free of pinholes. Preferably, the films are cured when exposed to temperatures of about 100° C. or greater, more preferably about 150° C. or greater and most preferably about 200° C. or greater. Preferably, the films cure at a temperature of about 300° C. or less.

In the preparation of the films, the composition may further comprise a catalyst suitable to facilitate or initiate the curing of the films. Such catalysts are well known in the art, for instance, for materials having ethylenic unsaturation, a free radical catalyst may be used. For aryl moieties with glycidyl ethers as end-groups, ureas, imidazoles and the like may be used. In the preparation of films from fluorenes with glycidyl ether aryl-terminal moieties, such materials may be reacted with commonly known curing agents which facilitate crosslinking. Among preferred curing agents are tetrahydrophthalic anhydride, nadic anhydride and maleic anhydride.

In another embodiment the 2,7-diaryl-9-substituted fluorenes and 9-substituted fluorene oligomers or polymers may be partially cured. This is known as B-staging. In such embodiment, the fluorenes and their oligomers or polymers thereof are exposed to conditions such that a portion of the reactive materials cure and a portion of the reactive materials do not cure. This is commonly used to improve the handleability of such a resin and can facilitate the preparation of the films. Such B-staged material can thereafter be used to prepare coatings by the means disclosed hereinbefore. Preferably, about 10 mole percent or greater of the reactive moieties are reacted. Preferably, about 50 mole percent or less of the reactive moieties are reacted.

SPECIFIC EMBODIMENTS

The following examples are included for illustrative purposes only and do not limit the scope of the claims. Unless otherwise stated, all parts and percentages are by weight.

EXAMPLE 1

2,7'-Dichloro-9,9-di(2-ethylhexyl)fluorene

To a stirred mixture of 2,7-dichlorofluorene (43 g, 0.183 mole) and 120 mL of dimethylsulfoxide (DMSO) under nitrogen was added benzyltriethylammonium chloride (2.3 g, 0.01 mole) and 60 mL of a 50 weight percent aqueous solution of sodium hydroxide. 2-Ethylhexyl bromide (85 g, 0.44 mole) was added and the mixture was agitated well for 2 hours. The reaction was exothermic, the temperature reaching 80° C. within 5 minutes after the addition of 2-ethylhexyl bromide and then falling off to 30° C. over the 2-hour reaction time. Analysis of an aliquot by high pressure liquid chromatography (HPLC) showed the complete disappearance of 2,7-dichlorofluorene and the formation of new product. Water (200 mL), and diethyl ether (250 mL) were added to the reaction mixture, stirred for 15 minutes and the layers were separated. The organic layer was washed with a saturated aqueous NaCl solution, water, dried (MgSO$_4$) and evaporated to remove ether. Fractional vacuum distillation of the residue provided 2,7-dichloro-9, 9-di(2-ethylhexyl)fluorene as clear liquid, boiling point 200° C./1 mm Hg, (79 g, 94 percent yield); HPLC analysis showed that the product was 99 percent pure; Proton Magnetic Spectrum (PMR) analysis was consistent with the title structure.

EXAMPLE 2

9,9-Di-n-butyl-2,7-dibromofluorene 2,7-Dibromofluorene (32.4 g, 0.1 mole), n-butyl bromide (75 g, 0.55 mole), tetra-n-butylammonium chloride (1.5 g) and 50 percent aqueous NaOH solution were stirred vigorously at 80° C. for 1 hour. The reaction mixture was allowed to cool to room temperature and extracted with ether. The ether extracts were washed with water and dried over anhydrous magnesium sulfate. Removal of solvent gave a yellow solid which was recrystallized from 400 mL of ethanol to provide 9,9-di-n-butyl-2,7-dibromofluorene as colorless crystals (42 g, 96 percent yield), melting point 120.5° C. to 121.5° C. HPLC analysis showed that the product had a purity of 99.5 percent and the proton and carbon-13 NMR were consistent with the title structure.

EXAMPLE 3

2,7-Dibromo-9,9-((2-methoxycarbonyl)ethyl) fluorene

To a 500 mL, three-necked, round-bottomed flask equipped with a condenser, magnetic stirring bar, stopper and a rubber septum was added 2,7-dibromofluorene (70.0 g, 0.216 mole) and methyl acrylate (166.0 g, 1.9 mole). To that stirring mixture was added dropwise (via syringe) benzyltrimethylammonium methoxide (3.3 mL, 40 weight percent solution). An exotherm was noted after addition of a few drops; temperature rose to ~60° C. After the addition was completed, the reaction was stirred for an additional 15 minutes.

Excess methyl acrylate was distilled off under reduced pressure. The crude product solidified after cooling to room temperature and was washed with hexane, then filtered. The crude solid was recrystallized from methanol to afford white crystals (79.0 g, 90 percent yield).

EXAMPLE 4

2,7-Dibromo-9,9-di(2-ethylhexyl)fluorene 2,7-Dibromo-9,9-di(2-ethylhexyl)fluorene, prepared by the procedure of Example 1, was obtained as a pale-yellow syrup in 93 percent yield after passing the crude product through a column of silica gel and eluting the product with hexane. The carbon and proton magnetic spectra were found to be consistent with the title structure.

EXAMPLE 5

2,7-Dichloro-9,9-di(3-methyl-1-butyl)fluorene

Following the procedure of Example 1, 2,7-dichloro-9,9-di(3-methyl-1-butyl)fluorene was prepared from 2,7-dichlorofluorene and 1-bromo-3-methylbutane as colorless crystals (recrystallized from pentane) in 90 percent yield, melting point 116° C. to 117.5° C. The spectral data were consistent with the title structure and HPLC analysis showed the purity as 99 percent and greater.

EXAMPLE 6

2,7-Dichloro-9,9-di(1-hexyl)fluorene 2,7-Dichloro-9,9-di(1-hexyl)fluorene was prepared from 2,7-dichlorofluorene and 1-bromohexane following the procedure of Example 1 as colorless crystals (recrystallized from hexane) in 91 percent yield; melting point 66° C. to 67° C. HPLC analysis showed that the sample was 99 percent or greater pure and the spectral data confirmed the title structure.

EXAMPLE 7

2,7-Dichloro-9-benzylidenylfluorene

To a stirred suspension of 2,7-dichlorofluorene (6.4 g, 27 mmole) in 30 mL of pyrrolidine or pyridine at 0° C. under nitrogen was added 6 mL of a 1M solution of tetrabutylammonium hydroxide in methanol. A solution of benzaldehyde (3.4 g, 32 mmole) in 25 mL of pyridine was then added over 10 minutes and the orange-colored mixture was allowed to stir at ambient temperature for 2 hours. The mixture was poured into 300 mL of ice-water, stirred for 3 hours, the yellow solid was filtered and recrystallized from n-heptane to provide 2,7-dichloro-9-benzylidenylfluorene as yellow needles, melting point 87° C. to 88° C. (7.8 g, 89.6 percent). PMR analysis was consistent with the title structure.

EXAMPLE 8

2,7-Dibromo-9-(4-dimethylaminobenzylidenyl) fluorene 2,7-Dibromo-9-(4-dimethylaminobenzylidenyl)fluorene was prepared using the procedure of Example 1 in 87.7 percent yield as light-orange powder, melting point 214° C. to 216° C. (recrystallized from toluene). PMR analysis is consistent with the title structure.

EXAMPLE 9

2,7-Dibromo-9-(4-(2-ethylhexyloxy)benzylidenyl) fluorene 2,7-Dibromo-9-(4-(2-ethylhexyloxy)benzylidenyl) fluorene was prepared using the procedure of Example 1 to give a yellow solid in 77 percent yield, melting point 68° C. to 70° C. PMR analysis was consistent with the title structure.

EXAMPLE 10

2,7-Dibromo-9-(3,5,5-trimethylhexylidenyl)fluorene

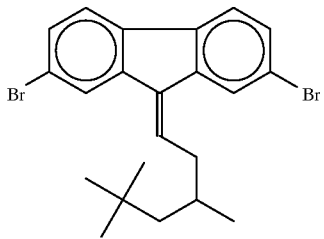

To a stirred mixture of 2,7-dibromofluorene (14 g, 40 mmole) and pyridine (40 mL) under nitrogen at −15° C. was added 8 mL of a 1M solution of tetrabutylammonium hydroxide in methanol. A solution of 3,5,5-trimethylhexanal (7.6 g, 53 mmole) in pyridine was added dropwise and the reaction mixture was stirred at ambient temperature overnight. The mixture was poured into 600 mL of ice-water, stirred for 1 hour, the pale yellow solid was isolated, and recrystallized from ethanol to provide the title compound as pale yellow powder, melting point 108° C. to 110° C. (11.6 g, 64.7 percent). PMR analysis was consistent with the assigned structure.

EXAMPLE 11

2,7-Dibromo-9-(5-norborn-2-enylidenyl)fluorene

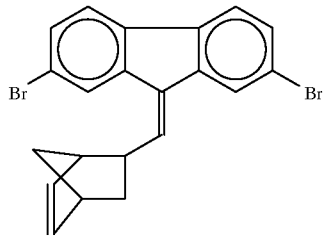

The title compound was prepared from 2,7-dibromofluorene and 5-norbornene-2-carboxaldehyde by following the procedure of Example 10. The product was extracted with ether and removal of ether gave a tan solid which was recrystallized from n-hexane to provide the title compound as tan crystals, melting point 118° C. to 120° C. (62 percent yield). PMR analysis and HPLC showed the title compound was obtained as a 1:1 mixture of exo and endo isomers.

EXAMPLE 12

Poly(9,9-di-n-hexylfluorenyl-2,7'-diyl)

A dried polymerization reactor was charged with 2,7-dichloro-9,9-di-n-hexylfluorene (4.03 g, 10.0 mmoles), nickel chloride-2,2'-bipyridine complex (Ni complex) (43 mg, 0.15 mmole), zinc dust (1.96 g, 30 mmoles) and triphenylphosphine (TPP) (1.31 g, 5 mmoles). The reactor was evacuated and filled with nitrogen several times, and finally filled with argon. Dry dimethylacetamide (DMAc) (10 mL) was added and the contents of the reactor were stirred and heated in an 80° C. oil bath. After 4 hours, a solid polymer cake was formed and the oil bath temperature was raised to 90° C. After about 5.75 hours, 10 mL of dry toluene was added and stirring and heating were continued. Two more 10 mL portions of toluene were added at 6.5 hours and 7.3 hours. Heating and stirring were continued for about 3.5 hours after the addition of the last portion of toluene. The mixture was poured into 150 mL of chloroform and filtered. The chloroform in the filtrate was removed on a rotary evaporator and the residue stirred with acetone. The large, bright-yellow granules obtained were dried for about 18 hours in a vacuum oven at 70° C. The yield was 3.10 g, 93.9 percent. The polymer had the following structure.

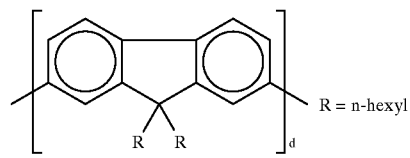

The inherent viscosity was 0.57 dL/g. Gel permeation chromatography showed Mw 39,630 Daltons, Mn 16,020 Daltons and polydispersity of 2.47. The degree of polymerization, d, was about 48. Differential scanning calorimetry (DSC) analysis at 5° C./minute showed two endothermic transitions centered at about 193° C. and 249° C., indicative of liquid crystallinity. There was no indication of glass transition.

For comparison, Fukuda's polymer of formally the same chemical composition had a polydispersity of 6.8, degree of polymerization relative to polystyrene of about 14, glass transition temperature of 55° C. and no crystallinity.

EXAMPLE 13

Poly(9,9-di-n-hexylfluorene-2,7'-diyl)

The experiment of Example 12 was repeated except the solvent was N-cyclohexylpyrrolidinone (20 mL). The polymerization was allowed to proceed for 18 hours and the product was purified and isolated as described in Example 12. The yield was 3.30 g, 100 percent. Inherent viscosity was 0.54 dL/g.

EXAMPLE 14

Poly(9,9-di-n-hexylfluorene-2,7'-diyl)

A dried polymerization reactor was charged with nickel chloride (52 mg, 0.4 mmole), 2,2'-bipyridine (62.4 mg, 0.4 mmole), zinc dust (5.76 g, 88 mmoles), and TPP (3.76 g, 14.0 mmoles). The reactor was evacuated and filled with nitrogen several times, and finally filled with argon. Dry DMAc (5 mL) was added and the content of the reactor stirred and heated in a 90° C. oil bath for 15 minutes to generate the active Ni(0) catalyst. A degassed solution of 2,7-dichloro-9,9-di-n-hexylfluorene (8.06 g, 20.0 mmoles) in 17 mL of dry DMAc was then added in two portions via a syringe and the polymerization was allowed to proceed for about 4.5 hours. The polymer isolated had inherent viscosity of 0.35 dL/g.

A thin film of the polymer was melted on a glass slide and examined on a hot-stage microscope under cross-polarized light. Intense birefringence was observed at above 200° C., indicating that the polymer undergoes a crystalline to liquid crystalline transition as suggested by DSC analysis.

EXAMPLE 15

Photoluminescence of Poly(9,9-di-n-hexylfluorene-2,7'-diyl)

A dilute chloroform solution of the polymer prepared in Example 14 was spin-coated onto a quartz plate to give a dense, uniform film. Photoluminescence spectrum was obtained by excitation at 381 nm. The light emitted was intensely blue: major maximum at 424 nm with minor maxima at 445 and 475 nm. The emission spectrum reported by Fukuda consists of a broad peak centered at about 495 nm and a very minor peak at about 425 nm. The differences in the emission spectra are consistent with the fact that Fukuda's polymer is substantially different from the polymer of this invention.

EXAMPLE 16

Poly(9,9-di-(4-t-butyldimethylsilyloxyphenyl) fluorene-2,7'-diyl)

To a reactor was added nickel chloride (27 mg, 0.2 mmole), 2,2'-bipyridine (34 mg, 0.22 mmole), zinc dust (1.5 g, 23 mmoles) and TPP (2.62 g, 10 mmoles). The reactor was evacuated and filled with argon several times. Dry DMAc (30 mL) was added and the contents stirred and heated in a 70° C. oil bath for about 1 hour to generate the active catalyst. 2,7-Dibromo-9,9-di-(4-t-butyldimethylsilyloxyphenyl)fluorene (7.36 g, 10.0 mmoles) was added and the polymerization allowed to proceed for 23 hours. The solid mass was slurried with tetrahydrofuran (THF) and the slurry filtered to remove inorganic substances. The THF solution was stripped on a rotary evaporator and the residue extracted with ether. The ether-insoluble polymer was obtained as a yellow, granular solid and had inherent viscosity of 0.28 dL/g. Gel permeation chromatography analysis showed Mw 31,120 Daltons and Mn 20,970 Daltons and polydispersity of 1.48. The polymer had the following structure.

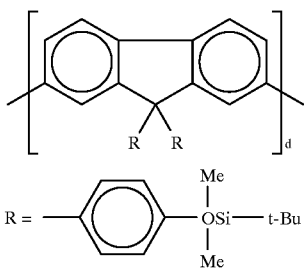

EXAMPLE 17

Poly(9,9-di-(4-(2-ethylhexanoyloxy)phenyl) fluorene-2,7'-diyl)

A reactor was charged with TPP (2.62 g, 10 mmoles), 2,7-dibromo-9,9-di-(4-(2-ethylhexanoyloxy)phenyl) fluorene (8.9 g, 11.7 mmoles), potassium iodide (0.22 g, 1.3 mmoles), DMAc (29 mL) and toluene (10 mL). Traces of moisture were removed as an azeotrope with toluene. The reactor was heated in an oil bath at 70° C. and stirred under argon, and to it nickel chloride (26 mg, 0.2 mmole) and zinc dust (2.0 g, 30 mmoles) were added. After about 20 hours, an additional portion of nickel chloride (20 mg) was added and the mixture allowed to react for another 24 hours. The solution was filtered to remove inorganic materials and the filtrate mixed with about 300 mL of ether. The product was collected as bright-yellow granules by filtration and washed with more ether and dried in a vacuum oven at 70° C. overnight. The polymer had an inherent viscosity of 0.37 dL/g, Mw 36,280 Daltons, Mn 20,700 Daltons, polydispersity of 1.75. The structure of the polymer is as follows.

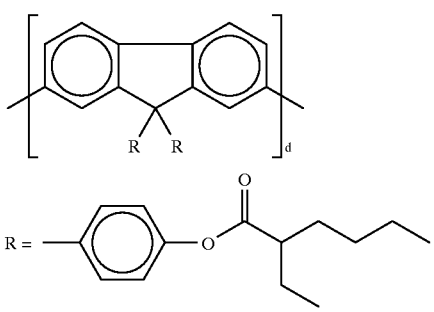

A solution of the resulting polymer in THF showed a broad absorption maximum at 389 nm, molar extinction coefficient of about 50,000 and photoluminescent peaks at 417, 439, and 473 nm in decreasing intensity.

EXAMPLE 18

Poly(9,9-di(2-ethylhexyl)fluorene-2,7'-diyl)

A reactor was charged with 2,7-dibromo-9,9-di(2-ethylhexyl)fluorene (2.75 g, 5 mmoles), zinc dust (0.98 g, 15 mmoles), a $NiCl_2$-bipyridine complex (21.5 mg, 0.075 mmole), and TPP (0.66 g, 2.5 mmoles). The reactor was evacuated and filled with nitrogen several times. N-cyclohexylpyrrolidinone (3 mL) was added and the contents were stirred under nitrogen in a 80° C. oil bath. After about 22 hours, the oil bath temperature was raised to 90° C. and the polymerization was allowed to proceed for a total of 31 hours. The reaction mixture was mixed with chloroform and filtered. The filtrate was concentrated and blended with methanol to give a yellow solid. The solid was dissolved in toluene (15 mL) and percolated through a short silica gel column with cyclohexane. The cyclohexane solution was concentrated and blended with methanol to precipitate the polymer as a yellow solid. Inherent viscosity was 0.15 dL/g. The structure of the polymer is as follows.

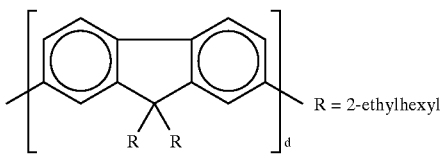

R = 2-ethylhexyl

A small piece of the polymer was melted on a microscope slide at 230° C. and slowly cooled to room temperature while being examined under cross-polarized light. Birefringence emerged at about 175° C. Heating the same film from room temperature revealed a liquid crystal to isotropic transition at about 165° C.

EXAMPLE 19

Copolymer

To a reactor was added 2,7-dichloro-9,9-di(2-ethylhexyl)fluorene (0.92 g, 2 mmoles), 2,7-dichloro-9,9-di-n-hexylfluorene (3.2 g, 8 mmoles), TPP (1.31 g, 5.0 mmoles), $NiCl_2$-bipyridine complex (43 mg, 0.15 mmole) and zinc dust (1.96 g, 30 mmoles). The reactor was evacuated and filled with nitrogen several times and then to it was added DMAc (10 mL). The mixture was stirred at 80° C. for 7 hours and at 90° C. for 15 hours. The reaction mixture was mixed with chloroform and filtered. The filtrate was concentrated and the copolymer precipitated in acetone and dried in a vacuum oven at 50° C. overnight. The structure of the copolymer is as follows.

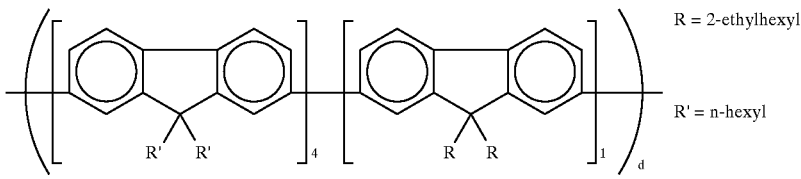

R = 2-ethylhexyl

R' = n-hexyl

The copolymer had an inherent viscosity of 0.35 dL/g and a Tg at about 89° C. as measured by DSC.

EXAMPLE 20

Poly(9,9-di(2-methoxycarbonylethyl)fluorene-2,7'-diyl)

A reactor was charged with TPP (2.0 g, 7.67 mmoles), zinc dust (2.02 g, 30.9 mmoles) and nickel bromide (0.22 g, 1.0 mmole). The reactor was evacuated and filled with nitrogen several times. To the reactor was added dimethylformamide (DMF) (5 mL) and the mixture was stirred at 40° C. for 15 minutes. Then a solution of 2,7-dibromo-9,9-di(2-methoxycarbonylethyl)fluorene (4.96 g, 10 mmoles) in DMF (10 mL), previously flushed with nitrogen, was added. The polymerization was allowed to proceed for 48 hours at 80° C. The reaction mixture was dissolved in chloroform and filtered. The chloroform layer was washed with water and dried over anhydrous magnesium sulfate. Upon removal of the solvent, a yellow granular solid was obtained with the following structure.

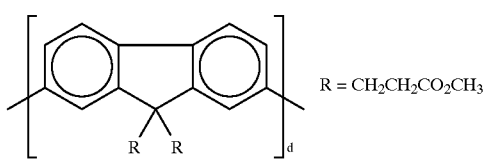

R = $CH_2CH_2CO_2CH_3$

EXAMPLE 21

Benzocyclobutene (BCB)-capped oligo(9,9-di(2-ethylhexyl)fluorene-2,7'-diyl)

A reactor was charged with 2,7-dibromo-9,9-di(2-ethylhexyl)fluorene (11.0 g, 20 mmoles), zinc dust (3.92 g, 60.0 mmoles), nickel complex (172 mg, 0.6 mmole) and TPP (2.62 g, 10 mmoles). The reactor was evacuated and filled with nitrogen several times. A solution of 4-bromobenzocyclobutene (Br—BCB) (1.10 g, 6 mmoles) in DMF (20 mL), previously flushed with nitrogen, was added to the reactor. The content was stirred at 75° C. under nitrogen for 24 hours. The reaction mixture was dissolved in about 50 mL of toluene and filtered and the filtrate washed with water. The toluene solution was stirred at room temperature with 5 mL of 70 percent t-butylhydroperoxide overnight. Excess peroxide was decomposed with aqueous sodium hydrogen sulfite and the toluene solution washed with water and evaporated to dryness. The residue was extracted with hexane separating the desired product from triphenylphosphine oxide. The hexane solution was percolated through a silica gel column and evaporated to give 5.1 g of the following resin.

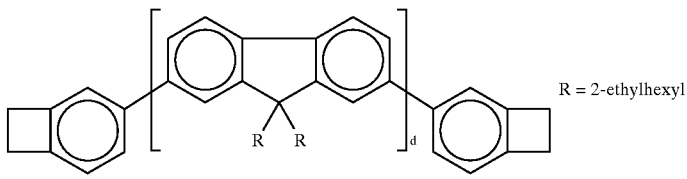

R = 2-ethylhexyl

Proton NMR analysis of the product indicated d=7.4.

A thin film of the material was examined on a hot-stage microscope under cross-polarized light. It was intensely birefringent, indicating presence of liquid crystallinity. Heating to 150° C. brought about the disappearance of birefringence, which re-emerged upon cooling to room temperature.

EXAMPLE 22

BCB-capped oligo(9,9-di(2-ethylhexyl)fluorene-2,7'-diyl)

The experiment described in Example 21 was repeated with 5.55 g (10.0 mmoles) of fluorene monomer, 0.54 g (3 mmoles) of Br—BCB, 1.91 g (29.2 mmoles) of zinc dust, 79 mmg (0.28 mmole) of nickel complex, 1.31 g (5 mmoles) of TPP and 10 mL of DMAc. The reaction was run at 80° C. for 16.5 hours. The product has the same structure as in Example 21 except d=7.2, as determined by proton NMR. A thin film of the resin was examined on a hot-stage microscope under cross-polarized light. The film was birefringent at room temperature, indicative of liquid crystallinity. Heating the film at 220° C. for 30 minutes and 250° C. for 1.5 hours gave an insoluble film, indicating that the BCB groups had substantially reacted, giving a crosslinked polymer.

EXAMPLE 23

BCB-capped oligo(9,9-di(2-ethylhexyl)fluorene-2,7'-diyl)

A 250 mL, three-necked, round-bottomed flask was charged with nickel chloride (0.156 g, 12 mmoles), 2,2'-bipyridine (0.188 g, 12 mmoles), TPP (5.24 g, 20 mmoles) and zinc dust (7.84 g, 120 mmoles) under nitrogen. 40 mL of DMAc was added via a syringe. The gray-colored slurry was stirred and heated at 80° C. for 15 minutes when the catalyst mixture turned reddish in color. A mixture of 2,7-dibromo-9,9-di(2-ethylhexyl)fluorene (21.94 g, 40 mmoles), Br—BCB (2.93 g, 16 mmoles), and 30 mL of DMAc was added to the catalyst dropwise over 15 minutes and the reaction mixture was stirred at 80° C. overnight.

The reaction mixture was cooled to room temperature, diluted with 200 mL of hexane and filtered through a bed of filter aid deatomaceous earth, and the filtered aid was washed with hexane (3×40 mL). To the filtrate was added 10 mL of a 70 percent t-butylhydroperoxide solution and the resulting mixture was stirred at room temperature overnight and filtered through a filter aid. The top hexane layer of the filtrate was recovered, washed with saturated NaCl solution, water and dried over $MgSO_4$. The hexane solution was concentrated to about 50 mL, cooled at 0° C. for a few hours to precipitate excess triphenylphosphine oxide, and the filtrate was evaporated to provide a yellow, semi-solid (16 g, 93 percent yield). The material was found to have a structure similar to that of Example 21 but with d=5.3.

Other properties of the material in the solid state were as follows: liquid crystallinity up to about 100° C.; strong UV absorption (λ max 365 nm); and photoluminescence at 419 nm with minor peaks at 447, 473, and 511 nm in decreasing intensity. A thin film was cured at 200° C. for 1 hour, 225° C. for 1 hour and 250° C. for 1 hour. The UV absorption of the film was essentially the same before and after cure but the major photoluminescent peak has shifted to 512 nm.

EXAMPLE 24

BCB-capped oligo(9,9-di-n-hexyl)fluorene-2,7'-diyl)

A reactor was charged with 2,7-dichloro-9,9-di-n-hexylfluorene (8.1 g, 20 mmoles), Br—BCB (1.1 g, 6 mmoles), nickel complex (172 mg, 0.6 mmole), zinc dust (3.92 g, 60 mmoles), TPP (2.62 g, 20 mmoles) and 30 mL of a 1:4 mixture of xylene and DMF. The reaction was stirred under nitrogen at 80° C. After about 1.5 hours, additional 10 mL of solvent mix was added and stirring was continued for 20 hours. The product mixture was dissolved in chloroform (100 mL) and filtered. Chloroform was removed under vacuum and the residue stirred with acetone (600 mL). The acetone-insoluble solid was isolated by filtration and dried in vacuo at 60° C. overnight to give 3.89 g of bright-yellow granules which was identified by proton NMR as follows.

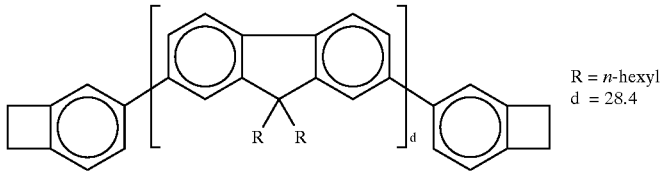

R = n-hexyl
d = 28.4

A solid film of this material showed UV absorption at 382 nm and photoluminescent peaks at 427, 440 and 481 nm in decreasing intensity.

The acetone solution was concentrated and mixed with ethanol (300 mL). The precipitated solid was isolated and dried to give 2.22 g of pale-yellow granules which was identified by proton NMR as follows.

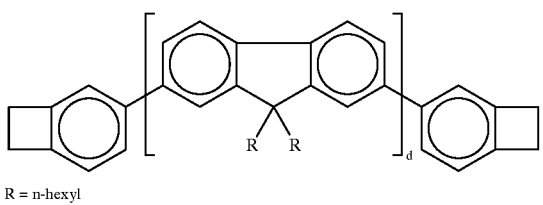

R = n-hexyl
d = 7.3

A solid film of this material showed UV absorption at 363 nm and photoluminescent peaks at 421, 442 and 475 nm in decreasing intensity.

Curing the above films as per the procedure of Example 22 did not bring about significant shifts in the emission wavelengths. DSC analysis of both materials showed the expected exotherms due to crosslinking reactions of BCB.

EXAMPLE 25

BCB-capped oligo(9,9-di(2-methoxycarbonylethyl) fluorene-2,7'-diyl)

A reactor was charged with 2,7-dibromo-9,9-di(2-methoxycarbonylethyl)fluorene (9.92 g, 20 mmoles), nickel complex (172 mg, 0.6 mmole), zinc dust (2.93 g, 60 mmoles) and TPP (2.62 g, 10 mmoles). It was evacuated and filled with nitrogen several times. To it was added a solution of Br—BCB (1.46 g, 8 mmoles) in DMAc (30 mL), previously flushed with nitrogen for 45 minutes. The mixture was stirred at 80° C. for about 20 hours. The reaction product was diluted with chloroform (300 mL) and filtered. The filtrate was concentrated and slurried with ethanol (300 mL) to give a fine, light-yellow solid which was filtered and washed with methanol. The product was dried in vacuum at 50° C. overnight. Proton NMR analysis indicated that the structure was as follows.

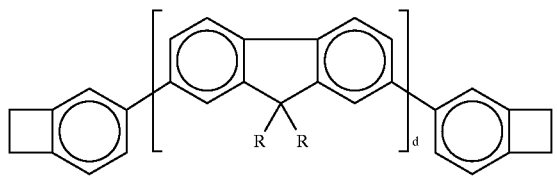

R = CH$_2$CH$_2$CO$_2$CH$_3$
d = 14.7

The resin showed multiple transitions during the first DSC scan from 25° C. to 300° C. A re-scan showed a Tg of about 151° C. A solid film of this material showed UV absorption at 368 nm and photoluminescent peak at 431 and 466 nm of about the same intensity, the latter being much broader. Curing the sample according to the procedure of Example 22 caused a shift of the emission peak to 540 nm.

EXAMPLE 26

BCB-capped oligo(9,9-di(2-ethylhexyl)fluorene-2,7'-diyl)

The experiment described in Example 21 was repeated with 37.9 g (60 mmoles) of 2,7-dibromo-9,9-di(2-ethylhexyl)fluorene, 11.8 g (180 mmoles) of zinc dust, 4.4 g (24 mmoles) of Br—BCB, 7.8 g (30 mmoles) of TPP, 0.52 g (1.8 mmoles) of nickel complex and 90 mL of DMAc. After 23 hours of reaction at 80° C., the content of the reactor was mixed with toluene and stirred with aqueous HCl to digest the excess zinc. The toluene solution was washed with water twice and evaporated to a yellow syrup which was dissolved in hexane (500 mL) and stirred overnight with 50 mL of 70 percent t-butylhydroperoxide. Excess peroxide was destroyed by stirring with an aqueous solution of sodium hydrogen sulfite and the hexane solution washed with water several times. The yellow oil obtained from evaporation of the solvent was passed through a short column (2-inch diameter and 2-inch height) of silica gel. The desired product was eluted with several liters of hexane. The combined hexane solution was again evaporated and the residue dissolved in about 80 mL of toluene. The toluene solution was poured as a thin stream into 1.2 L of stirred methanol. The solid cake deposited was collected, dissolved in hexane and the solution dried over anhydrous magnesium sulfate. The solution was evaporated to leave an oil which was further stripped of volatile components at about 90° C., 0.5 mm Hg, yielding 14.8 g of BCB-capped oligomer with the following structure.

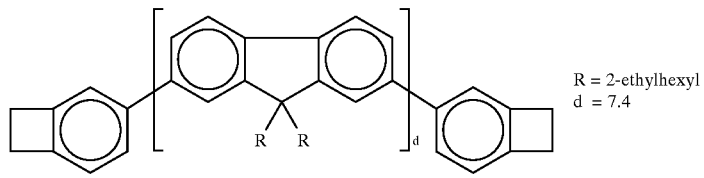

R = 2-ethylhexyl
d = 7.4

A one-gram sample of the material was placed in a round-bottom flask which was alternately evacuated and filled with argon several times. The flask was then placed in an oil bath heated to 150° C. and evacuated to about 0.3 mm Hg for 30 minutes. After filling the flask with argon, the temperature of the bath was raised to 180° C. The sample was heated at this temperature for 24 hours and was allowed to cool under argon. DSC analysis showed that about 44 percent of the BCB groups had reacted during the B-staging process. A xylene solution of the B-staged resin was used to spin-coat a quartz disk. The disk was heated in a nitrogen-purged oven from 25° C. to 250° C. at a ramp rate of 3° C./minute and held at 250° C. for 1 hour. This provided a highly photoluminescent (blue), smooth, crosslinked film essentially free of pin-holes and other defects.

EXAMPLE 27

Hydroxyphenyl-capped oligo(9,9-di(2-ethylhexyl) fluorene-2,7'-diyl)

Example 21 was repeated with 19 g (30 mmoles) of 2,7-dibromo-9,9-di(2-ethylhexyl)fluorene, 6 g (90 mmoles) of zinc dust, 3.45 g (12 mmoles) of 4-bromophenyl-t-butyldimethylsilyl ether, 3.9 g (15 mmoles) of TPP, 0.26 g (0.9 mmole) of nickel complex and 50 mL of DMAc. The reaction was allowed to proceed at 80° C. for 21 hours. The reaction mixture was diluted with toluene (about 200 mL) and filtered through a filter aid to remove unreacted zinc. The filtrate was removed of toluene on a rotary evaporator and the residue shaken with water and extracted with hexane. The hexane solution was filtered through a filter aid again and the filtrate stirred with 15 mL of 70 percent t-butylhydroperoxide overnight. Excess peroxide was decomposed with aqueous sodium hydrogen sulfite and the solution washed repeatedly with water. Triphenylphosphine oxide was removed by filtration and the hexane solution was dried over anhydrous magnesium sulfate. Evaporation of hexane and further stripping of volatiles at 0.5 mm Hg, 120° C., 1 hour, gave a semi-solid. This was dissolved in toluene (about 60 mL) and the toluene solution poured as a thin stream into methanol. The semi-solid precipitated cake was dissolved in hexane. The hexane solution yielded 10.0 g of strongly photoluminescent (blue) semi-solid after drying and stripping. The NMR spectrum of this material is consistent with the expected structure as follows.

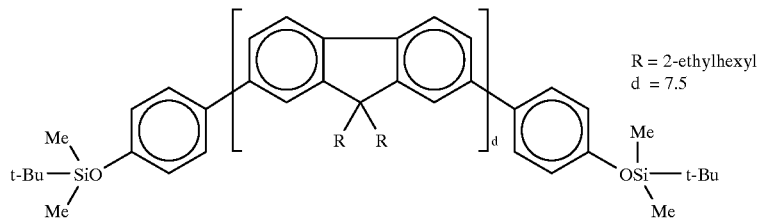

The above material was refluxed with a solution of tetrahydrofuran (100 mL) and concentrated HCl (5 mL) for 6 hours to effect desilylation. The NMR spectrum of the product was consistent with the expected structure as follows.

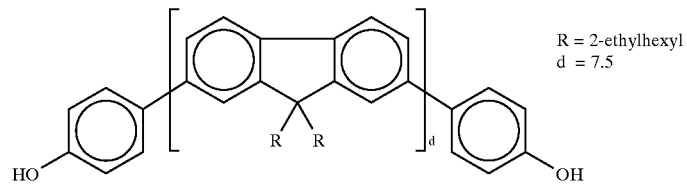

EXAMPLE 28

Cyanatophenyl-capped oligo(9,9-di(2-ethylhexyl) fluorene-2,7'-diyl)

The phenolic material from Example 27 (6.5 g) was dissolved in methylene chloride (75 mL) and mixed with 2.5 g of cyanogen bromide in a reactor. The resulting solution was cooled to about −20° C. and to it was added a solution of 3 mL triethylamine and 10 mL methylene chloride over a period of about 3 minutes. The mixture was stirred at −10° C. for 1 hour and was then washed with dilute HCl, water and dried over anhydrous magnesium sulfate. Removal of solvent gave 6.5 g of light-brown oil showing the expected infrared absorption bands (2200 to 2300 cm$^{-1}$) for cyanate groups and no absorption band for phenolic groups. The oil was further purified by passage through a short silica gel column to give a strongly photoluminescent (blue), yellow semi-solid. The NMR and infrared spectra of the material are consistent with the following structure.

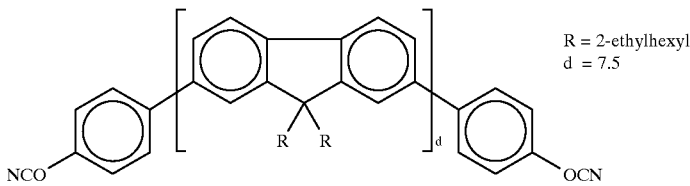

R = 2-ethylhexyl
d = 7.5

EXAMPLE 29

Polymerization of 2,7-dichloro-9-benzylidinylfluorene

To a dry reactor equipped with a mechanical stirrer, rubber septa, and an inlet connected to a vacuum and nitrogen manifold was added TPP (2.00 g, 8 mmoles), zinc dust (3.02 g, 31 mmoles), and nickel complex (0.26 g, 1 mmole). The reactor was evacuated and purged with nitrogen 7 times and was heated to 40° C. 1-Methyl-2-pyrrolidinone (NMP) (10 mL) was added via a syringe. The reaction mixture was stirred at approximately 250 rpm. After a few minutes, the solution turned to a reddish-brown color. To the reaction mixture was added a solution of 2,7-dichloro-9-benzylidenylfluorene (3.23 g, 10 mmoles) in NMP (7.0 mL). The reaction was stirred at 80° C. for 48 hours.

The reaction mixture was poured into acetone (300 mL) to precipitate the polymer. The orange-gray precipitate was collected and washed with acetone (2×100 mL). After drying in air, the solid was crushed to a powder and the powder was slowly added to 250 mL of 3N HCl. The mixture was stirred for 3 hours, at which point the precipitate was a bright-orange color. The solid was collected, washed with water (3×100 mL) then air-dried overnight. The solid was then dried in a vacuum oven at 60° C. overnight to afford 2.46 g (98 percent yield) of an orange powder. Based on the yield and spectral data, the structure of the polymer was as follows.

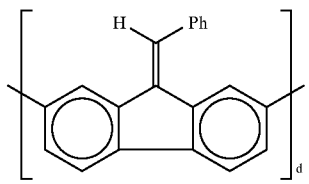

A film of the polymer, cast onto a quartz disk from a chloroform solution, showed a strong UV absorption band centered at 368 nm and a broad photoluminescent band centered at 571 nm.

EXAMPLE 30
Copolymerization (1:1) of 2,7-dichloro-9-benzylidenylfluorene and 2,7-dichloro-9,9-n-hexylfluorene The procedure of Example 29 was repeated with 1.62 g (5 mmoles) of 2,7-dichloro-9-benzylidenylfluorene and 2.02 g (5 mmoles) 2,7-dichloro-9,9-di-n-hexylfluorene in DMAc (15.0 mL). The reaction mixture was stirred at 80° C. for 48 hours. The reaction mixture was added to methylene chloride (200 mL) and the resulting solution was filtered through a plug of filter aid to remove the unreacted zinc. The filtered solution, after concentration, was slowly added to acetone (300 mL) to precipitate the product. The bright-yellow precipitate was collected and washed with acetone (3×50 mL) and dried to give 1.79 g of 1:1 copolymer whose structure could be alternating as shown below or could consist of blocks of the two monomeric units. A film, cast on a quartz disk from a chloroform solution, showed a strong UV absorption band centered at 370 nm and photoluminescent bands centered at 417 and 551 nm

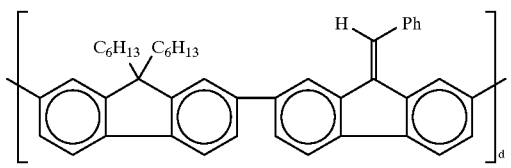

EXAMPLE 31
Copolymerization (1:4) of 2,7-dichloro-9-benzylidenylfluorene and 2,7'-dichloro-9,9-di-n-hexylfluorene Example 30 was repeated with 0.65 g (2 mmoles) of 2,7-dichloro-9-benzylidenylfluorene and 3.23 g (8 mmoles) of 2,7'-dichloro-9,9-di-n-hexylfluorene in NMP (15 mL). The reaction mixture was stirred at 80° C. for 48 hours and was then added to methylene chloride (200 mL). The methylene chloride solution was filtered through a plug of filter aid to remove the zinc. The filtered solution, after concentration, was slowly added to acetone (200 mL) to give 1.0 g of yellow polymer. The acetone solution was concentrated and slowly added to ethanol (200 mL) to precipitate an additional portion of polymeric product (1.3 g). Based on the yield and spectral data, the structure of the polymer is as follows.

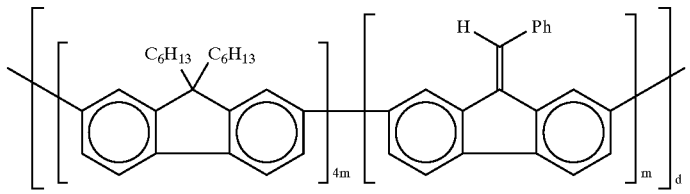

A film, cast on a quartz disk from a chloroform solution, showed a strong UV absorption band centered at 370 nm and photoluminescent bands centered at 470 and 522 nm.

EXAMPLE 32

Polymerization of 2,7-dichloro-9-(3,5,5-trimethylhexylidenyl)fluorene

The procedure of Example 29 was repeated with 4.5 g (10 mmoles) of 2,7-dichloro-9-(3,5,5-trimethylhexylidenyl) fluorene in DMF (15 mL). The reaction mixture was stirred at 80° C. for 28 hours. The reaction mixture was added to acetone (200 mL) to precipitate the product. The precipitate was collected, air dried, crushed to a powder, then added to an aqueous solution of 3N HCl (300 mL). The mixture was stirred for 3 hours to dissolve the zinc metal. The bright, yellow-orange precipitate was collected, washed with methanol (3×100 mL), acetone (3×100 mL) and dried to give 2.5 g of product. The product was soluble in hot 1,2-dichlorobenzene. The melting point was 306° C.

EXAMPLE 33

Polymerization of 2,7-dichloro-9-(5-norbornenylid-2-ene)fluorene

The procedure of Example 29 was repeated with 4.3 g (10 mmoles) of 2,7-dichloro-9-(5-norbornenylid-2-ene)fluorene in DMF (20 mL). The reaction mixture was stirred at 80° C. for 26 hours. The reaction mixture was added to acetone (200 mL) to precipitate the product. The precipitate was collected, air dried, crushed to a powder, then added to an aqueous solution of 3N HCl (300 mL). The mixture was stirred for 3 hours to dissolve the zinc metal. The precipitate was collected, washed with methanol (3×100 mL), acetone (3×100 mL) and dried to give 3.0 g of product.

What is claimed is:

1. A polyfluorene compound comprising from about 3 to about 10,000 repeat units of the formula

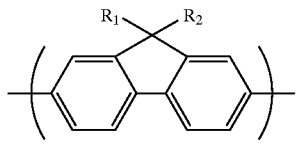

wherein $R_1$ is an aliphatic group including at least one polar heteroatom-containing group and $R_2$ is selected from the group consisting of hydrogen, alkyls and aliphatic groups including at least one polar heteroatom-containing group, the compound being essentially devoid of polynuclear structures and substitutions at positions other than the 2,7-position of the formula.

2. The polyfluorene compound of claim 1 wherein $R_2$ is an alkyl.

3. The polyfluorene compound of claim 1 wherein $R_2$ is a lower alkyl including at least one heteroatom-containing polar group.

4. The polyfluorene compound of claim 1 wherein the heteroatom-containing group $R_1$ is selected from oxygen-containing groups, nitrogen-containing groups and sulfur-containing groups.

5. The polyfluorene compound of claim 4 wherein $R_1$ is a cyano alkyl.

6. In a light-emitting organic solid state device in which an active layer comprising an electrically activated luminescent organic polymer is positioned between a hole-injecting electrode and an electron-injecting electrode, the improvement comprising employing a polymer of claim 1 as the electrically activated luminescent organic polymer.

7. The light-emitting device of claim 6 configured as a light-emitting diode.

8. The light-emitting device of claim 6 configured as a light-emitting electrochemical cell.

9. A method for generating light comprising applying a solid-state device activating voltage across the hole injecting electrode and electron injecting electrodes of the device of claim 6, thereby giving rise to light emission from the device's layer of electroluminescent organic polymer and detecting the emitted light.

10. A polyfluorene compound comprising from about 3 to about 5,000 repeat units of the formula

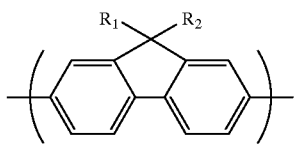

wherein $R_1$ is an aliphatic group including at least one polar heteroatom-containing group and $R_2$ is selected from the group consisting of hydrogen, alkyls and aliphatic groups including at least one polar heteroatom-containing group, the compound being essentially devoid of polynuclear structures and substitutions at positions other than the 2,7-position of the formula.

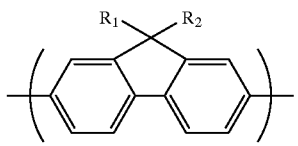

11. In a light-emitting organic solid state device in which an active layer comprising an electrically activated luminescent organic polymer is positioned between a hole-injecting electrode and an electron-injecting electrode, the improvement comprising employing a polymer of claim 10 as the electrically activated luminescent organic polymer.

* * * * *